(12) United States Patent
Tari et al.

(10) Patent No.: US 7,704,962 B1
(45) Date of Patent: Apr. 27, 2010

(54) SMALL OLIGONUCLEOTIDES WITH ANTI-TUMOR ACTIVITY

(75) Inventors: Ana M. Tari, Houston, TX (US); Gabriel Lopez-Berestein, Bellaire, TX (US); Yolanda Gutierrez-Puente, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 954 days.

(21) Appl. No.: 09/506,979

(22) Filed: Feb. 18, 2000

Related U.S. Application Data

(63) Continuation-in-part of application No. 09/381,747, filed as application No. PCT/US97/18348 on Oct. 3, 1997, now Pat. No. 7,285,288.

(51) Int. Cl.
*A01N 43/04* (2006.01)
*C12Q 1/68* (2006.01)
*C12N 15/58* (2006.01)
*C07H 21/02* (2006.01)
*C07H 21/04* (2006.01)

(52) U.S. Cl. .................... 514/44; 435/6; 435/91.31; 435/458; 536/23.1; 536/24.5

(58) Field of Classification Search .................. 435/6, 435/91.1, 455, 325, 375, 91.31, 458; 514/44; 536/23.1, 24.5

See application file for complete search history.

(56) References Cited

U.S. PATENT DOCUMENTS

| | | | |
|---|---|---|---|
| 4,229,360 A | 10/1980 | Schneider et al. | 260/403 |
| 4,394,448 A | 7/1983 | Szoka, Jr. et al. | 435/172 |
| 4,469,863 A | 9/1984 | Ts'o et al. | 536/27 |
| 4,480,041 A | 10/1984 | Myles et al. | 436/508 |
| 4,721,612 A | 1/1988 | Janoff et al. | 424/1.21 |
| 4,835,263 A | 5/1989 | Nguyen et al. | 536/27 |
| 4,837,028 A | 6/1989 | Allen | 424/450 |
| 4,904,582 A | 2/1990 | Tullis | 435/6 |
| 4,920,016 A | 4/1990 | Allen et al. | 424/450 |
| 4,924,624 A | 5/1990 | Suhadolnik et al. | 514/44 |
| 4,950,432 A | 8/1990 | Mehta et al. | 264/4.6 |
| 5,015,568 A | 5/1991 | Tsujimoto et al. | 435/5 |
| 5,030,442 A | 7/1991 | Uster et al. | 424/45 |
| 5,049,388 A | 9/1991 | Knight et al. | 424/450 |
| 5,087,617 A | 2/1992 | Smith | 514/44 |
| 5,094,785 A | 3/1992 | Law et al. | 264/4.3 |
| 5,098,890 A | 3/1992 | Gewirtz et al. | 514/44 |
| 5,100,662 A | 3/1992 | Bolcsak et al. | 424/450 |
| 5,112,962 A | 5/1992 | Letsinger et al. | 536/25.3 |
| 5,135,917 A | 8/1992 | Burch | 514/44 |
| 5,178,875 A | 1/1993 | Lenk et al. | 424/450 |
| 5,188,897 A | 2/1993 | Suhadolnik et al. | 428/402.2 |
| 5,202,429 A | 4/1993 | Tsujimoto et al. | 536/23.5 |
| 5,227,170 A | 7/1993 | Sullivan | 424/450 |
| 5,248,671 A | 9/1993 | Smith | 514/44 |
| 5,264,618 A | 11/1993 | Felgner et al. | 560/224 |
| 5,271,941 A | 12/1993 | Cho-Chung | 424/450 |
| 5,279,833 A | 1/1994 | Rose | 424/450 |
| 5,279,957 A | 1/1994 | Gross | 435/348 |
| 5,320,962 A | 6/1994 | Stiles et al. | 435/252.3 |
| 5,324,654 A | 6/1994 | Bredesen | 435/376 |
| 5,376,646 A | 12/1994 | Pittrof et al. | 514/78 |
| 5,378,825 A | 1/1995 | Cook et al. | 536/25.34 |
| 5,417,978 A | 5/1995 | Tari et al. | 424/450 |
| 5,459,251 A | 10/1995 | Tsujimoto et al. | 536/23.5 |
| 5,525,719 A | 6/1996 | Srivastava et al. | 536/26.7 |
| 5,527,538 A | 6/1996 | Baldeschwieler | 424/1.21 |
| 5,539,085 A | 7/1996 | Bischoff et al. | 530/350 |
| 5,539,094 A | 7/1996 | Reed et al. | 536/23.5 |
| 5,560,923 A | 10/1996 | Rahman et al. | 424/450 |
| 5,565,337 A | 10/1996 | Diamond et al. | 435/70.2 |
| 5,583,034 A | 12/1996 | Green et al. | 435/240.2 |
| 5,622,852 A | 4/1997 | Korsmeyer | 435/325 |
| 5,641,662 A * | 6/1997 | Debs et al. | 435/6 |
| 5,661,018 A | 8/1997 | Ashley et al. | 435/172.3 |
| 5,665,710 A | 9/1997 | Rahman et al. | 514/44 |
| 5,696,248 A | 12/1997 | Peyman et al. | 536/22.1 |
| 5,705,385 A | 1/1998 | Bally et al. | 435/320.1 |

(Continued)

FOREIGN PATENT DOCUMENTS

CA 2171589 3/1996

(Continued)

OTHER PUBLICATIONS

Verma et al. Nature, vol. 389, pp. 238-243, 1997.*
Crystal, R.G. Science, vol. 270, pp. 404-410, 1995.*
Crooke, S.T. Antisense Res. and Application, Chapter 1, pp. 1-50, published by Springer-Verlag, 1998.*
Branch, A. Trends in Biochem. Sci., vol. 23, pp. 45-50, 1998.*
Friedmannj, T. Scientific American, June Volume, pp. 96-101, 1997.*
Natalie Milner et al., Selecting effective antisense reagents on combinatorial oligonucleotide arrays, Nature Biotechnology, vol. 15, Jun. 1997, pp. 537-541.*

(Continued)

*Primary Examiner*—Jane Zara
(74) *Attorney, Agent, or Firm*—Fulbright & Jaworski L.L.P.

(57) ABSTRACT

The present invention provides short antisense oligonucleotide compositions and methods for their use in the treatment of Bcl-2-associated diseases like cancer, such as follicular lymphoma (FL). The antisense oligonucleotides contain sequences that hybridize to Bcl-2 nucleic acids, the gene products of which are known to interact with the tumorigenic protein Bcl-2. The use of novel short antisense oligonucleotides, from 7 bases to 9 bases in length, is described in this invention. The invention also describes certain specific sequences which are longer than 9 bases and are 11 or 15 bases long. Used alone, or in conjunction with other antisense oligonucleotides, these antisense oligonucleotide compositions inhibit the proliferation of cancer cells.

17 Claims, 5 Drawing Sheets

U.S. PATENT DOCUMENTS

| | | | | |
|---|---|---|---|---|
| 5,734,033 | A | | 3/1998 | Reed ........................ 536/23.1 |
| 5,750,669 | A | | 5/1998 | Rosch et al. ............... 536/24.3 |
| 5,756,122 | A | | 5/1998 | Thierry et al. .............. 424/450 |
| 5,817,811 | A | | 10/1998 | Breipohl et al. ............. 544/264 |
| 5,831,048 | A | | 11/1998 | Schwighoffer et al. ..... 536/23.1 |
| 5,831,066 | A | * | 11/1998 | Reed ........................ 536/23.1 |
| 5,837,838 | A | | 11/1998 | Reed et al. ................. 536/23.1 |
| 5,855,911 | A | * | 1/1999 | Lopez-Berestein et al. .. 424/450 |
| 5,874,224 | A | | 2/1999 | Bandman et al. ............... 435/6 |
| 5,891,714 | A | | 4/1999 | Ashley et al. ............ 435/320.1 |
| 5,908,635 | A | | 6/1999 | Thierry ....................... 424/450 |
| 5,976,567 | A | * | 11/1999 | Wheeler et al. ............. 424/450 |
| 5,981,501 | A | * | 11/1999 | Wheeler et al. ............... 514/44 |
| 5,989,912 | A | * | 11/1999 | Arrow et al. ................ 435/375 |
| 6,015,886 | A | | 1/2000 | Dale et al. ................. 536/23.1 |
| 6,030,954 | A | * | 2/2000 | Wu et al. ...................... 514/44 |
| 6,034,235 | A | | 3/2000 | Sugiyama et al. .......... 536/24.5 |
| 6,040,181 | A | * | 3/2000 | Reed ........................ 435/377 |
| 6,042,846 | A | * | 3/2000 | Lopez-Berestein et al. .. 424/450 |
| 6,096,720 | A | | 8/2000 | Love et al. .................... 514/44 |
| 6,110,490 | A | | 8/2000 | Thierry ....................... 424/450 |
| 6,120,794 | A | | 9/2000 | Liu et al. ..................... 424/450 |
| 6,120,798 | A | | 9/2000 | Allen et al. ................. 424/450 |
| 6,126,965 | A | | 10/2000 | Kasid et al. ................. 424/450 |
| 6,136,965 | A | | 10/2000 | Bruice et al. ............... 536/25.3 |
| 6,211,162 | B1 | | 4/2001 | Dale et al. ..................... 514/44 |
| 6,211,349 | B1 | | 4/2001 | Dale et al. ................. 536/23.1 |
| 6,277,832 | B1 | | 8/2001 | Sugiyama et al. ............. 514/44 |
| 6,277,981 | B1 | | 8/2001 | Tu et al. .................... 536/25.3 |
| 6,291,668 | B1 | | 9/2001 | Ziegler et al. .............. 536/24.5 |
| 6,326,487 | B1 | | 12/2001 | Peyman et al. ............. 536/24.5 |

FOREIGN PATENT DOCUMENTS

| | | | |
|---|---|---|---|
| DE | | 4110085 | 3/1991 |
| EP | | 0 252 685 | 1/1988 |
| WO | WO 88/04924 | | 7/1988 |
| WO | WO 89/06977 | | 8/1989 |
| WO | WO 90/09180 | | 8/1990 |
| WO | WO 90/10488 | | 9/1990 |
| WO | WO 91/16901 | | 11/1991 |
| WO | WO 92/21330 | | 12/1992 |
| WO | WO 93/07883 | | 4/1993 |
| WO | WO 93/11245 | | 6/1993 |
| WO | WO 93/20200 | | 10/1993 |
| WO | WO 93/24653 | | 12/1993 |
| WO | WO 94/04545 | | 3/1994 |
| WO | WO 94/05259 | | 3/1994 |
| WO | WO 95/03788 | | 2/1995 |
| WO | WO 95/08350 | | 3/1995 |
| WO | WO 95/28497 | | 10/1995 |
| WO | WO 96/27663 | | 9/1996 |
| WO | WO 96/40062 | | 12/1996 |
| WO | WO 97/07784 | * | 6/1997 |
| WO | WO 98/14172 | | 4/1998 |
| WO | WO 98/56905 | | 12/1998 |
| WO | WO 00/40595 | | 7/2000 |
| WO | WO 02/17852 | | 3/2002 |

OTHER PUBLICATIONS

W. James, Towards gene-inhibition therapy: a review of progress and prospects in the field of antiviral antisense nucleic acids and ribozymes, Antiviral Chemistry & Chemotherapy (1991) 2(4). pp. 191-214.*

Agrawal et al. Molecular Medicine Today, Feb. 2000, vol. 6, pp. 72-81.*

Pihl-Carey, I. BioWorld Today, Dec. 1999, vol. 10, pp. 1-2.*

Chirila et al. Biomaterials, 2002, vol. 23, pp. 321-342.*

Palu et al. Biotech. 1999, vol. 68, pp. 1-13.*

Tamm et al. The Lancet. Aug. 2001, vol. 358, pp. 489-497.*

Tormo et al. Proceedings of the Amer. Assoc. for Cancer Res. Annual Meeting, 1996, vol. 37, p. 173, Abstract No. 1190.*

Konopleva et al. J. of the Amer. Society of Hematology, vol. 92, No. 10, Suppl 1, Part 1 of 2, Nov. 15, 1998, Abstract No. 2100.*

Reed, J.C. et al. Proc. Natl. Acad. Sci. vol. 87: 3660-3664 (1990).*

Miyake, H. et al. Cancer Res. vol. 59: 4030-4034 (1999).*

Branch, A., Trends in Biochem. Sci., vol. 23, pp. 45-50 (1998).*

Crooke, S., Antisense Res. and Applica., Chapter 1, pp. 1-50, ed. by S. Crooke, published by Springer-Verlag.*

Agrawal, S. et al., Molecular Med. Today, vol. 6, pp. 72-81 (2000).*

Peracchi, A. Rev. Med. Virol., vol. 14, pp. 47-64 (2004).*

Reed et al, Annal of Oncology, vol. 5, Suppl. 1, S61-S65 (1994).*

Reed et al., Proc. Natl. Acad. Sci., vol. 87, pp. 3660-3664 (1990).*

Reed et al., Annals of Oncology, vol. 5, Suppl 1, S61-S65 (1994).*

Aisenberg, "Coherent view of non-Hodgkin's lymphoma," *J. Clin. Oncol.*, 13(10):2656-2675, 1995.

Akhtar et al., "Interactions of antisense DNA oligonucleotide analogs with phospholipids membranes (liposomes)," *Nucleic Acids Res.*, 19(20):5551-5559, 1991.

Baichwal and Sugden, "Vectors for gene transfer derived from animal DNA viruses: Transient and stable expression of transferred genes," *In*: Kucherlapati R, (ed.) Gene transfer. New York: Plenum Press, pp. 117-148, 1986.

Bakhshi et al., "Cloning the chromosomal breakpoint of t(14;18) human lymphomas: clustering around $J_H$ on chromosome 14 and near a transcriptional unit on 18," *Cell*, 41:899-906, 1985.

Bangham et al., "Diffusion of univalent ions across the lamellae of swollen phospholipids," *J. Mol. Biol.*, 13:238-252, 1965.

Benvenisty and Reshif, "Direction introduction of genes into rats and expression of the genes," *Proc. Nat'l Acad. Sci. USA*, 83:9551-9555, 1986.

Boise et al., "*bcl-X*, a *bcl*-2-related gene that functions as a dominant regulator of apoptotic cell death," *Cell*, 74:597-608, 1993.

Campos et al., "Effects of *BCL-2* antisense oligodeoxynucleotides on in vitro proliferation and survival of normal marrow progenitors and leukemic cells," *Blood*, 84(2):595-600, 1994.

Chang et al., "Foreign gene delivery and expression in hepatocytes using a hepatitis B virus vector," Abstract, *Hepatology*, 14(4):124A, 1991.

Chen and Okayama, "High-efficiency transfection of mammalian cells by plasmid DNA," *Mol. Cell Biol.*, 7(8):2745-2752, 1987.

Chittenden et al., "Induction of apoptosis by the Bcl-2 homologue Bak," *Nature*, 374:733-736, 1995.

Coffin, "Retroviridae: the viruses and their replication," *In: Virology*, Fields et al. (eds.), New York: Raven Press, pp. 1767-1847, 1996.

Cotter et al., "Antisense oligonucleotides suppress B-cell lymphoma growth in a SCID-hu mouse model," *Oncogene*, 9:3049-3055, 1994.

Coupar et al., "A general method for the construction of recombinant vaccinia virus expressing multiple foreign genes," *Gene*, 68:1-10, 1988.

Deamer and Uster, "Liposome Preparation: Methods and Mechanisms," *Liposomes*, M. Ostro ed. (1983).

Dubensky et al., "Direct transfection of viral and plasmid DNA into the liver or spleen of mice," *Proc. Nat'l Acad. Sci. USA*, 81:7529-7533, 1984.

Fecheimer et al., "Transfection of mammalian cells with plasmid DNA by scrape loading and sonication loading," Abstract, *Proc. Nat'l Acad. Sci. USA*, 84(23):8463-8467, 1987.

Fraley et al., "Entrapment of a bacterial plasmid in phospholipid vesicles: potential for gene transfer," *Proc. Nat'l Acad. Sci. USA*, 76(7):3348-3352, 1979.

Friedman et al., "CCAAT/enhancer-binding protein activates the promoter of the serum albumin gene in cultured hepatoma cells," *Genes & Devel.* 3:1314-1322, 1989.

Ghosh and Bachhawat, "Targeting of liposomes to hepatocytes," *In*: Wu G. Wu C ed., Liver diseases, targeted diagnosis and therapy using specific receptors and ligands, New York: Marel Dekker, pp. 87-103, 1991.

Gopal, "Gene transfer method for transient gene expression, stable transformation, and cotransformation of suspension cell cultures," *Mol. Cell Biol.*, 5:1188-1190, 1985.

Graham and van der Eb, "A new technique for the assay of infectivity of human adenovirus 5 DNA", *Virology*, 52:456-467, 1973.

Graham et al., "Characteristics of a human cell line transformed by DNA from human adenovirus type 5," *J. Gen. Virol.*, 36:59-72, 1977.

Graninger et al., "Expression of Bcl-2 and Bcl-2-Ig fusion transcripts in normal and neoplastic cells," *J. Clin. Invest.*, 80:1512-1515, 1987.

Harland and Weintraub, "Translation of mammalian mRNA injected into *Xenopus oocytes* is specifically inhibited by antisense RNA," *J. Cell Biol.*, 101:1094-1099, 1985.

Hermonat and Muzycska, "Use of adeno-associated virus as a mammalian DNA cloning vector: Transduction of neomycin resistance into mammalian tissue culture cells," *Proc. Nat'l Acad. Sci. USA*, 81:6466-6470, 1984.

Hockenbery et al., "Bcl-2 is an inner mitochondrial membrane protein that blocks programmed cell death," *Nature*, 348:334-336, 1990.

Horwich et al., "Synthesis of hepadnavirus particles that contain replication-defective duck hepatitis B virus genomes in cultured HuH7 cells," *J. Virol.* 64(2):642-650, 1990.

Johnson et al., "Patterns of survival in patients with recurrent follicular lymphoma: a 20-year study from a single center," *J. Clin. Oncol.*, 13(1):140-147, 1995.

Kaneda et al., "Increased expression of DNA cointroduced with nuclear protein in adult rat liver," *Science*, 243:375-378, 1989.

Kato et al., "Expression of hepatitis B virus surface antigen in adult rat liver," *J. Biol. Chem.*, 266(6):3361-3364, 1991.

Kiefer et al., "Modulation of apoptosis by the widely distributed Bcl-2 homologue Bak," *Nature*, 374: 736-739, 1995.

Kitada et al., "Investigations of antisense oligonucleotides targeted against *bcl-2* RNAs," *Antisense Res. Dev.*, 3:157-169, 1993.

Klein et al., "High-velocity microprojectiles for delivering nucleic acids into living cells," *Nature*, 327:70-73, 1987.

Kozopas et al "*MCL-1*, a gene expressed in programmed myeloid cell differentiation, has sequence similarity to *BCL-2*," *Proc. Nat'l Acad. Sci. USA*, 90:3516-3520, 1993.

Lin et al., "Characterization of A1, a novel hemopoietic-specific early-response gene with sequence similarity to *BCL-2*," *J. Immunol.*, 151(4):1979-1988, 1993.

Mann et al., "Construction of a retrovirus packaging mutant and its uses to produce helper-free defective retrovirus," *Cell*, 33:153-159, 1983.

McDonnell and Korsmeyer, "Progression from lymphoid hyperplasia to high-grade malignant lymphoma in mice transgenic for the t(14;18)," *Nature*, 349-:254-256, 1991.

McDonnell et al., "*bcl-2*-immunoglobulin transgenic mice demonstrate extended B cell survival and follicular lymphoproliferation," *Cell*, 57:79-88, 1989.

McDonnell, "The bcl-2-immunoglobulin transgenic mouse: a model of the t(14;18) translocation in human follicular lymphoma," *Transgene*, 1:47-52, 1993.

Neilan et al., "An African Swine fever virus with similarity to the protooncogene *bcl-2* and the Epstein-Barr virus gene *BHRF1*," *J. Virol.*, 67(7):4391-4394, 1993.

Nicolas and Rubenstein, "Retroviral vectors," *In: Vectors: A survey of molecular cloning vectors and their uses*, Rodriguez and Denhardt, (eds.), Stoneham: Butterworth, pp. 494-513, 1988.

Nicolau and Sene, "Liposome-mediated DNA transfer in eukaryotic cells: dependence of the transfer efficency upon the type of liposomes used and the host cell cycle stage," *Biochem. Biophys. Acta*, 721:185-190, 1982.

Nicolau et al., "Liposomes as carriers for in vivo gene transfer and expression," *Methods Enzymol.*, 149:157-176, 1987.

Nuñez et al., "Deregulated Bcl-2 gene expression selectively prolongs survival of growth factor-deprived hemopoietic cell lines," *J. Immunol.*, 144(9):3602-3610, 1990.

Oltvai et al., "Bcl-2 heterodimerizes in vivo with a conserved homolog, bax, that accelerates programmed cell death," *Cell*, 74:609-619, 1993.

Paskind et al., "Dependence of moloney murine leukemia virus production on cell growth," *Virology*, 67:242-248, 1975.

Pearson et al., "Identification of an Epstein-Barr virus early gene encoding a second component of the restricted early antigen complex," *Virology*, 160:151-161, 1987.

Potter et al., "Enhancer-dependent expression of human κ immunoglobulin genes introduced into mouse pre-B lymphocytes by electroporation," *Proc. Nat'l Acad. Sci. USA*, 81:7161-7165, 1984.

Reed et al., "Antisense-mediated inhibition of *bcl-2* protooncogene expression and leukemic cell growth and survival: comparisons of phosphodiester and phosphorothioate oligodeoxynucleotides," *Cancer Research*, 50: 6565-6570, 1990.

Reed et al., "*BCL2*-mediated tumorigenicity in a human T-lymphoid cell line: synergy with *MYC* and inhibition by *BCL2* antisense," *Proc. Nat'l Acad. Sci. USA*, 87:3660-3664, 1990.

Reed, "Bcl-2: prevention of apoptosis as a mechanism of drug resistance," *Hematol. Oncol. Clin. North Am.*, 9(2):451-473, 1995.

Ridgeway, "Mammalian expression vectors," *In*: Rodriguez RL, Denhardt DT, (ed.) Vectors: A survey of molecular cloning vectors and their uses. Stoneham: Butterworth, pp. 467-492, 1988.

Rippe et al., "DNA-mediated gene transfer into adult rat hepatocytes in primary culture," *Mol. Cell Biol.*, 10(2):689-695, 1990.

Sato et al., "Interactions among members of the Bcl-2 protein family analysed with a yeast two-hybrid system," *Proc. Nat'l Acad. Sci. USA*, 91:9238-9242, 1994.

Stratford-Perricaudet and Perricaudet, "Gene transfer into animals: the promise of adenovirus," pp. 51-61, *In: Human Gene Transfer*, Eds, O. Cohen-Haguenauer and M. Boiron Editions John Libbey Exrotext, France, 1991.

Szoka and Papahadjopoulos, "Procedude for preparation of liposimes with large internal aqueous space and high capture by reverse-phase evaporation," *Proc. Nat'l Acad. Sci. U.S.A.* 75(9):4194-4198, 1978.

Tari et al., "Liposomal delivery of methylphosphonate antisense oligodeoxynucleotides in chronic myelogenous leukemia," *Blood*, 84(2):601-607, 1994.

Temin, "Retrovirus vectors for gene transfer: Efficient integration into and expression of exogenous DNA in vertebrate cell genome," *In: Gene Transfer*, Kucherlapati (ed.), New York: Plenum Press, pp. 149-188, 1986.

Tsujimoto and Croce, "Analysis of the structure, transcripts, and protein products of *bcl-2*, the gene involved in human follicular," *Proc. Natl. Acad. Sci. USA*, 83:5214-5218, 1986.

Tsujimoto et al., "Characterization of the protein product of *bcl-2*, the gene involved in human follicular lymphoma," *Oncogene*, 2:3-7, 1987.

Tsujimoto et al., "The t(14;18) chromosome translocation involved in B-cell neoplasms result from mistakes in VDJ joining," *Science*, 229:1390-1393, 1985.

Tur-Kaspa et al., "Use of electroporation to introduce biologically active foreign genes into primary rat hepatocytes," *Mol. Cell Biol.*, 6(2):716-718, 1986.

Wagner et al., "Antisense gene inhibition by pligonucleotides containing C5 propyne pyrimidines," *Science*, 260:1510-1513, 1993.

Wong et al., "Appearance of β-lactamase activity in animal cells upon liposome mediated gene transfer," *Gene*, 10:87-94, 1980.

Wu and Wu, "Evidence for targeted gene delivery to Hep G2 hepatoma cells in vitro," *Biochemistry*, 27:887-892, 1988.

Wu and Wu, "Receptor-mediated in vitro gene transformations by a soluble DNA carrier system," *J. Biol. Chem.*, 262(10):4429-4432, 1987.

Yang et al., "Bad, a heterodimeric partner for Bcl-$X_L$ and Bcl-2, displaces Bax and promotes cell death," *Cell*, 80:285-291, 1995.

Yang et al., "In vivo and in vitro gene transfer to mammalian somatic cells by particle bombardment," *Proc. Nat'l Acad. Sci. USA*, 87:9568-9572, 1990.

Yin et al., "BH1 and BH2 domains of Bcl-2 are required for inhibition of apoptosis and heterodimerization with Bax," *Nature*, 369: 321-323, 1994.

Zelenin et al., "High-velocity mechanical DNA transfer of the chloramphenicolacetyl transferase gene into rodent liver, kidney and mammary gland cells in organ explants and in vivo," *FEBS Lett.*, 280(1):94-96, 1991.

Cotter et al., "Human Bcl-2 antisense therapy for lymphomas," *Biochimica et Biophysica Acta*, 1489:97-106, 1999.

Gleave et al., "Targeting bcl-2 gene to delay androgen-independent progression and enhance chemosensitivity in prostate cancer using antisense bcl-2 oligodeoxynucleotides," *Urology*, 54(Suppl 6A):36-46, 1999.

Jansen et al., "bcl-2 antisense therapy chemosensitizes human melanoma in SCID mice," *Nature Medicine*, 4(2):232-234, 1998.

Ziegler et al., "Induction of apoptosis in small-cell lung cancer cells by an antisense oligodeoxynucleotide targeting the Bcl-2 coding sequence," *J. Nat'l Cancer Institute*, 89(14):1027-1036, 1997.

Abubakr et al., Effectiveness of Bcl-2 antisense oliogodeoxynucleotides (AS-ODN) against human follicular small-cleaved cell lymphoma (FSCCL)-SCID mice xenograft model, *Blood*, 84 (10 Suppl. 1) 374A, 1994.

Agrawal, "Antisense oligonucleotides: towards clinical trials," *TIB Tech*, 14(10):376-387, 1996.

Agris et al., "Inhibition of vesicular stomatitis virus protein synthesis and infection by sequence-specific oligodeoyribonucleoside methylphosphonates," *Biochemistry*, 25:6268-6275, 1986.

Akhtar et al., "Release of antisense oligdeoynucleotide analogues from liposomes: implications for cellular transport and drug delivery," 128$^{th}$ Meeting of British Pharmaceutical Conference 1991, United Kingdom, Sep. 10-13, 1991, *J. Pharm. Pharmacol.*, 43 (Suppl.):Abstract 24P, 1991.

Aktar et al., "Lipsome Delivery of Antisense Methylphosphonate and Phosphorothioate Oligonucleotides: A Study with MLV, FATMLV, and LUV Liposomes," *Proceed. Intern. Symp. Control. Rel. Bioact. Mater.*, 19:345-346, 1992.

Allsopp et al., "The Proto-Oncogene bcl-2 Can Selectively Rescue Neurotrophic Factor-Dependent Neurons from Apoptosis," *Cell*, 73:295, 1993.

Almazan et al., "Methylphosphate-containing oligonucleotides efficiently and specifically inhibit bcl-2 and erb-2 expression in vitro," *Proc. Amer. Assoc. Cancer Res.*, 37:353, 1996.

Arad et al., "Use of reconstituted sendai virus envelopes for fusion-mediated microinjection of double-stranded RNA: Inihibition of protein synthesis in interferon-treated cells," *Biochimica et Biophysica Acta*, 859:88-94, 1986.

Bennett et al., "Cationic lipids enhance cellular uptake and activity of phosphorothioate antisense oligonucleotides," *Molecular Pharmacology*, 41(6):1023-1033, 1992.

Boiziau et al., "Modified oligonucleotides in rabbit reticulocytes: uptake, stability and antisense properties," Biochimie, 73:1403-1408, 1991.

Borzillo et al., "*Bcl-2* Confers Growth and Survival Advantage to Interleukin 7-dependent Early Pre-B Cells Which Become Factor Independent by a Multistep Process in Culture," *Oncogene*, 7:869, 1992.

Braasch and Corey, "Novel antisense and peptide nucleic acid strategies for controlling gene expression," *Biochemistry*, 41(14):4503-4510, 2002.

Bradbury et al., "Down-Regulation of bcl-2 in AML Blasts by All-Trans Retinoic Acid and Its Relationship of CD34 Antigen Expression," British Journal of Haemaltology, 94:671-675, 1996.

Budker et al., "Cell membranes as barriers for antisense constructions," *Antisense Research and Development*, 2:177-184, 1992.

Capaccioli et al., "Cationic lipids improve antisense oligonucleotide uptake and prevent degradation in cultured cells and in human serum," *Biochemical and Biophysical Research Communications*, 197(2):818-825, 1993.

Capaccioli et al., "A bcl-2/IgH Antisense Transcript Deregulates bcl-2 Gene Expression in Human Follicular Lymphoma t(14;18) Cell Lines," Oncogene, 13:105-115, 1996.

Cazals-Hatem et al., "Molecular Cloning and DNA Sequence Analysis of cDNA Encoding Chicken Homologue of the Bcl-2 Oncoprotein," *Biochim. Biophys. Acta*, 1132:109, 1992.

Chang et al., "Foreign gene delivery and expression in hepatocytes using a hepatitis B virus vector," Abstract, *Hepatology*, 14(4):124A, 1991.

Chao, et al., "Bcl-x$_L$ and Bcl-2 Repress a Common Pathway of Cell Death," *J. Exp. Med.*, 182:821-828, 1995.

Cheng et al., "Bax-independent inhibition of apoptosis by Bcl-x$_L$," *Nature*, 279:554-556, 1996.

Chen-Levy and Cleary, "Membrane Topology of the Bcl-2 Protooncogenic Protein Demonstrated in Vitro," *J. Biol. Chem.* 265:4929, 1990.

Chen-Levy et al., "The *bcl-2* Candidate Proto-Oncogene Product Is a 24-Kilodalton Integral-Membrane Protein Highly Expressed in Lymphoid Cell Lines and Lymphomas Carrying the t(14;18) Translocation," *Mol. Cell. Biol.*, 9:701, 1989.

Choi et al., "The role of bcl-X$_L$ in CD40-mediated rescue from anti-μ-induced apoptosis in WEHI-231 B lymphoma cells," *Eur. J. Immunol.*, 25:1352-1357, 1995.

Citro et al., "Chemical modification of ligands for cell receptors to introduce foreign compounds into the cells," *Colon & Rectum*, 37(2):S127-S132, 1994.

Clarenc et al., "Delivery of Antisense Oligonucleotides by poly(L-Lysine) Conjugation and Liposome Encapsulation," *Anti-Cancer Drug Design*, 8:81-94, 1993.

Clarke et al., "A recombinant *bcl-x$_S$* adenovirus selectively induces apoptosis in cancer cells but not in normal bone marrow cells," *Proc. Natl. Acad. Sci. USA*, 92:11024-11028, 1995.

Cleary et al., "Cloning and Structural Analysis of cDNAs for *bcl-2* and a Hybrid *bcl-2*/Immunoglobulin Transcript Resulting from the t(14:18) Translation," *Cell*, 47:19, 1986.

Cuende et al., Programmed cell death by bcl-2-dependent and independent mechanisms in B lymphoma cells, *EMBO J.*, 12:1555-1560, 1993.

Datta et al., "Overexpression of Bcl-x$_L$ by Cytotoxic Drug Exposure Confers Resistance to Ionizing Radiation-induced Internucleosomal DNA Fragmentation," *Cell Growth & Differentiation*, 6:363-370, 1995.

Dole et al., "Bcl-x$_L$ Is Expressed in Neuroblastoma Cells and Modulates Chemotherapy-Induced Apoptosis," *Cancer Res.*, 55:2576-2582, 1995.

Duke et. al, "Morphological, biochemical and flow cytometric assays of apoptosis," *In*: Coligan et. al (eds) Current protocols in immunology, vol. I., New York: John Wiley & sons, p. 3.17.1, 1991.

Eguchi et al., "Isolation and Characterization of the Chicken *bcl-2* Gene: Expression in a Variety of Tissues Including Lymphoid and Neuronal Organs in Adult and Embryo," *Nucl. Acids. Res.*, 20:4187, 1992.

Far et al., "Concepts to automate the theoretical design of effective antisense oligonucleotides," *Bioinformatics*, 17(11):1058-1061, 2001.

Frankowski et al., "Function and expression of the *Bcl-x* gene in the developing and adult nervous system," *NeuroReport*, 6:1917-1921, 1995.

Garcia et al., "Prevention of Programmed Cell Death of Sympathetic Neurons by the *bcl-2* Prot-Oncogene," *Science*, 258:302, 1992.

Gerwirtz et al., "Facilitating oligonucleotide delivery: helping antisense delivery on its promise," *Proc. Natl. Acad. Sci U.S.A.*, 93: 3161-3163, 1996.

Gomez-Manzano et al., "Bax, Bcl-2 and p53 Interactions Modulate p53-Induced Apoptosis in Glioma Cells," *Proceedings of the American Association for Cancer Research*, 37:204, Abstract 1397, Mar. 1996.

González-García et al., "*bcl-x* is expressed in embryonic and postnatal neural tissues and functions to prevent neuronal cell death," *Proc. Natl. Acad. Sci. USA.*, 92:4304-4308, 1995.

González-García et al., "*bcl-x$_L$* is the major *bcl-x* mRNA form expressed during murine development and its product localizes to mitochondria," *Development*, 120:3033-3042, 1994.

Gottschalk et al., "Identification of immunosuppressant-induced apoptosis in a murine B-cell line and its prevention by bcl-x but not bcl-2," *Proc. Natl. Acad. Sci. USA.*, 91:7350-7354, 1994.

Gottschalk et al., "The ability of Bcl-x$_L$ and Bcl-2 to prevent apoptosis can be differentially regulated," *Death and Differentiation*, 3:113-118, 1996.

Grever and Chabner, "Cancer Drug Discovery and Developoment," *Cancer Principles & Practice of Oncology, 5$^{th}$ Edition*, Lippicott-Raven Publishers, 19:385-394, 1997.

Grillot et al., "*bcl-x* Exhibits Regulated Expression During B Cell Development and Activation and Modulates Lymphocyte Survival in Transgenic Mice," *J. Exp. Med.*, 183:381-391, 1996.

Gura, "Antisense has growing pains," *Science*, 270:575-577, 1995.

Jäättelä et al., "Bcl-x and Bcl-2 inhibit TNF and Fas-induced apoptosis and activation of phospholipase A$_2$ in breast carcinoma cells," *Oncogene*, 10:2297-2305, 1995.

Jasty et al., "*bcl-x$_L$*, A Gene Which Regulates Programmed Cell Death, Is Expressed In Neuroblastoma Tumor Cell Lines (abstract)," *Clinical Res.*, 42:416A, 1994.

Juliano et al., "Lipsomes as a Drug Delivery System for Antisense Oligodeoxynucleotides Encapsulated by Liposomes," *Antisense Research and Development*, 2:165-176, 1992.

Keller et al., "Synthesis and hybridization properties of oligonucleotides containing 2'-O-modified ribonucleotides," *Nucleic Acids Research*, 21(19):4499-4505, 1993.

Krajewski et al., "Immunohistochemical Analysis of In Vivo Patterns of Bcl-x Expression," *Cancer Res.*, 54:5501-5507, 1994.

Kramer et al., "Self-specific T lymphocyte lines as vehicles for gene therapy: myelin specific T cells carrying exogenous nerve growth factor gene (abstract)," *J. Cell. Biochem.*, Suppl. O (17 Part E):215, 1993.

Krieg et al., "Modification of antisense phosphodiester oligodeoynucleotides by a 5' cholesteryl moiety increases cellular association and improves efficacy," *Proc. Natl. Acad. Sci., USA*, 90:1048-1052, 1993.

Ledley, "Non-viral gene therapy," *Curr. Opin. Biotechnol.*, 5:626-636, 1994.

Leonetti et al., "Antibody-targeted liposomes containing oligodeoyribonucleotides complementary to viral RNA selectively inhibit viral replication," *Proc. Natl. Acad. Sci. USA*, 87:2448-2451, 1990.

Loke et al., "Characterization of oligonucleotide transport into living cells," *Proc. Natl. Acad. Sci. USA*, 86:3474-3478, 1989.

Loke et al., "Delivery of *c-myc* Antisense Phosphorothioate Oligodeoxynucleotides to Hematopoietic Cells in Culture by Lipsome Fusion: Specific Reduction in *c-myc* Protein Expression Correlates with Inhibition of Cell Growth and DNA Synthesis," *Current Topics in Microbiology and Immunology, Mechanisms in B-Cell Neoplasis*, 141:282-289, 1988.

Marin et al., "Complementation and Cell Death Regulation By Bcl-2, p53 and c-myc During In Vivo Lymphomagenesis," *Journal of Cellular Biochemistry*, Supplement 19B, p. 286, Abstract B8-224, Feb. 5-Mar. 15, 1995.

Martiat et al., "Retrovirally transduced antisense sequences stably suppress P210$^{BCR-ABL}$ epression and inhibit the proliferation of BCR/ABL-containing cell lines," *Blood*, 81(2):502-509, 1993.

Masserano et al., "Dopamine Induces Apoptotic Cell Death of a Catecholaminergic Cell Line Derived from the Central Nervous System," Molecular Pharmacology, 50:1309-1315, 1996.

McCarthy et al., "Apoptosis in the development of the immune system: Growth factors, clonal selection and *bcl-2*," *Cancer Metastasis Reviews*, 11:157-178, 1992.

McDonnell et al., "Cell Death Suppression by Bcl-2 Is Associated with Altered Nuclear-Cytoplasmic Trafficking," *Proceedings of the American Association for Cancer Research*, 37:16, Abstract 111, Mar. 1996.

Miller et al., "Gene Transfer and antisense nucleic acid techniques," *Parasitology Today*, 10(3):92-97, 1994.

Miller, "Oligonucleoside methylphosphonates as antisense reagents," *Bio/Technology*, 9:358-362, Apr. 1991.

Minn et al., "Expression of Bcl-$x_L$ can Confer a Multidrug Resistance Phenotype," *Blood*, 86:1903-1910, 1995.

Miyashita et. al, "Tumor suppressor p53 is a regulator of bcl-2 and bax gene expression in vitro and in vivo," *Oncogene*, 9:1799, 1994.

Moody et al., "Regiospecific inhibition of DNA duplication by antisense phosphate-methylated oligodeoynucleotides," *Nucleic Acids Research*, 17(12):4769-4782, 1989. (Abstract).

Núñez et al., "BCL-X is expressed in embryonic and adult neuronal tissues and its expression prevents neuronal cell death (abstract)," *J. Cell. Biochem.*, Supplement 0 (19B), B8-438, p. 317, 1995.

Oppenheim et al., "Brain-derived neurotrophic factor rescues developing avian motoneurons from cell death," *Nature*, 360:755-757, 1992.

Pocock et al., "In vivo supresion of B-cell lymphoma Bcl-2 antisense oligonucleotides," *Blood*, 82 (Suppl. 1), 200A, 1993.

Raff, M.C., "Social controls on cell survival and cell death," *Nature*, 356:397-400, 1992.

Reed et al., "Regulation of *bcl-2* Proto-Oncogene Expression During Normal Human Lymphocyte Proliferation," *Science*, 236:1295, 1987.

Renneisen et al., "Inhibition of epression of human immunodeficiency virus-1 in vitro by antibody-targeted liposomes containing antisense RNA to the *env* region," *The Journal of Biological Chemistry*, 265(27):16337-16342, 1990.

Rojanasakul, "Antisense oligonucleotide therapeutics: drug delivery and targeting," *Advanced Drug Delivery Reviews*, 18:115-131, 1996.

Ropert et al., "Inhibition of the Friend Retrovirus by Antisense Oligonucleotides Encapusulated in Liposomes: Mechanism Action," *Pharmaceutical Research*, 10(10):1427-1433, Apr. 1993.

Schendel et al., "Channel Formation by Antiapoptotic Protein Bcl-2," Proc. Natl. Acad. Sci. USA, 94:5113-5118, 1997.

Schott et al., "Bcl-$x_L$ protects cancer cells from p53-mediated apoptosis," *Oncogene*, 11(7):1389-1394, 1995.

Schott, et al., "BCL-$X_L$ Protects Cells from P53-Mediated Apoptosis", *Journal of Investigative Medicine* 43 (SUPPL. 3) 458A, 1995.

Sedlak et al., "Multiple Bcl-2 family members demonstrate selective dimerization with Bax," *Proc. Nat'l Acad. Sci. USA*, 92:7834, 1995.

Sentman et al., "bcl-2 Inhibits Multiple Forms of Apoptosis but Not Negative Selection in Thymocytes," *Cell*, 67:879, 1991.

Shea et al., "Synthesis, hybridization properties and antiviral activity of lipid-oligodeoynucleotide conjugates," *Nucleic Acids Research*, 18(13):3777-3783, 1990.

Siegel et al., "Inhibition of thymocyte apoptosis and negative and antigenic selection in *bcl-2* transgenic mice," *Proc. Natl. Acad. Sci. USA*, 89:7003, 1992.

Skorski et al., "Gene-targeted Specific Inhibition of Chronic Myeloid Leukemia Cell Growth by BCR-ABL Antisense Oligodeoxynucleotides," *Folia Histochemica et Cytobiologica*, 29(3):85-90, 1991.

Stein et al., "Oligodeoynucleotides as inhibitors of gene expression: A review," *Cancer Research*, 48(10):2635-2944, 1988.

Stein et al., "Antisense oligonucleotides as therapeutic agents—is the bullet really magical?" *Science*, 261:1004-1012, 1993.

Strasser et al., "bcl-2 Transgene Inhibits T Cell Death and Perturbs Thymic Self-Censorship," *Cell*, 67:889, 1991.

Strasser et al., "Enforced *BCL2* Expression in B-lymphoid Cells Prolongs Antibody Responses and Elicits Autoimmune Disease," *Proc. Natl. Acad. Sci. USA*, 88:8661, 1991.

Stull et al., "Antigene, ribozyme and aptamer nucleic acid drugs: progress and prospects, pharmaceutical research," 12(4):465-483, 1995.

Sumantran et al., "Overexpression of Bcl-$x_S$ Sensitizes MCF-7 Cells to Chemotherapy-Induced Apoptosis," *Cancer Res.*, 55:2507-2510, 1995.

Szczylik et al., Selective inhibition of leukemia cell proliferation by BCR-ABL antisense oligodeoynucleotides,,Science, 253:562-565, 1991.

Taj et al., "Inhibition of P210$^{BCR/ABL}$ epression in K562 cells by electroporation with an Antisense oligonucleotide," *Leukemia and Lymphoma*, 3:201-208, 1990.

Thierry et al., "Liposomal delivery as a new approach to transport antisense oligonucleotides," *Gene Regulation, Biology of Antisense RNA and DNA*, 1: 147-161, 1992.

Thierry et al., Intracellular Availability of Unmodified, Phosphorothioated and Liposomally Encapsulated Oligodeoxynucleotides for Antisense Activity, *Nucleic Acids Research*, 20(21):5691-5698, Sep. 1992.

Thierry et al., "Modulation of multidrug Resistance by Antisense Oligodeoxynucleotides Encapsulated by Liposomes," *Proceedings of the American Association for Cancer, Preclinical Pharmacology/Experimental Therapeutics*, Abstract 2578, 32:443, May 1991.

Thierry et al., Overcoming Multidrug Resistance in Human Tumor Cells Using Free and Liposomally Encapsulated Antisense Oligodeoxynucleotides,: *Biochemical and Biophysical Research Communications*, 190(3):952-960, Feb. 1994.

Thompson, C. B., "Apoptosis in the Pathogenesis and Treatment of Disease," *Science*, 267:1456-1462, 1995.

Tidd et al., "Evaluation of N-*ras* oncogene anti-sense, sense and nonsense sequence methylphosphonate oligonucleotide analogues," *Anti-Cancer Drug Design*, 3:117-127, 1988.

Tidd et al., "Partial protection of oncogene, anti-sense oligodeoynucleotides against serum nuclease degradation using terminal methylphosphonate groups," *Be. J. Cancer*, 60:343-350, 1989.

Tormo et al., "Antitumor activity of liposomal-bcl-2-antisense oligonucleotides in follicular lymphoma (abstract)," *Proc. Am. Assoc. Cancer. Res.*, 37:1190, 1996.

Tsuchida et al., "Iron-ligand bonding properties of synthetic iron-porphyrin complees with oygen transporting ability in aqueous media," *J. Chem. Soc. Dalton Transactions*, 10:2455-2458, 1987.

Uhlmann et al., "Antisense oligonucleotides: a new therapeutic princpal," *Chemical Reviews*, 90(4):543-584, 1990.

Vasanthakumar et al., "Modulation of drug resistance in a daunorubicin resistant subline with oligonucleoside methylphosphonates," *Cancer Communications*, 1(4):225-232, 1989.

Vaux et al., "*Bcl-2* gene promotes haemopoietic cell survival and cooperates with *c-myc* to immortalize pre-B cells," *Nature*, 335:440, 1988.

Wagner, "Gene inhibition using antisense oligodeoynucleotides," *Nature*, 372:333-335, 1994.

Webb et al., "Extrathymic Tolerance of Mature T Cells: Clonal Elimination as a Consequence of Immunity," *Cell*, 63:1249, 1990.

Weber-Nordt et al., "Interleukin-10 Increases Bcl-2 Expression and Survival in Primary Human CD34+ Hematopoietic Progenitor Cells," *Blood*, 88(7):2549-2558, 1996.

Weiss, "Upping the antisense ante scientists bet on profits from reverse genetics," *Science News*, 139:108-109, 1991.

Wickstrom, "Antisense DNA therapeutics neutral analogs and their stereochemistry," *Raven Press Ser. Mol. Cell. Biol.*, 1:119-132, 1992.

Williams, G.T., "Programmed Cell Death: Apoptosis and Oncogenesis," *Cell*, 65:1097-1098, 1991.

Wrone-Smith, et al., "Discordant Expression of Bcl-x and Bcl-2 by Keratinocytes in Vitro and Psoriatic Keratinocytes in Vivo," *Am. J. Pathology*, 146:1079-1088, 1995.

Wu-Pong, "Oligonucleotides: Opportunities for drug therapy and research, pharmaceutical technology," 18:102-114, 1984.

Yeoman et al., "Lipofectin enhances cellular uptake of antisense DNA while inhibiting tumor cell growth", *Antisense Research and Development*, 2:51-59, 1992.

Zhang et al., "Gene therapy for the peripheral nervous system rat neuritogenic T cell line carry mouse nerve growth factor gene (abstract)," *J. Cell. Biochem.*, Suppl. 0 (17 Part E):SZ-116, 1993.

Zhang et al., "BCL2 Regulates Neural Differentiation," Proc. Natl. Acad. Sci. USA, 93:4504-4508, 1996.

Zon, "Pharmaceutical considerations," *Oligodeoxynucleotides*, Jack S. Cohen, Ed., CRC Press, 11:233-247, 1989.

Miller et al., "Synthesis of oligodeoxyribonucleotide ethyl phosphotriesters and their specific complex formation with transfer ribonucleic acid," *Biochemistry*, 13(24):4887-4896, 1974.

\* cited by examiner

SMALL OLIGONUCLEOTIDES WITH ANTI-TUMOR ACTIVITY

The present application is a continuation-in-part of U.S. Ser. No. 09/381,747, filed Sep. 22, 1999, now U.S. Pat. No. 7,285,288 which was a US nationalization of PCT/US97/18348, filed Oct. 3, 1997 and U.S. Ser. No. 08/726,211, filed Oct. 4, 1996.

BACKGROUND OF THE INVENTION

1. Field of the Invention

The present invention relates generally to the fields of cancer therapy. More particularly, the invention concerns the use of small antisense oligodeoxynucleotides for antitumor therapy.

2. Description of Related Art

The bcl-2 gene has been associated with a wide variety of diseases such as hematologic malignancies and includes both leukemias and lymphomas and more specifically includes follicular and nonfollicular lymphomas, chronic lymphocytic leukemia, and plasma cell dyscrasias (Campos et al., 1994); solid tumors like those associated with breast, prostate and colon cancer; and immune disorders. One particular Bcl-2-related disease is Follicular non-Hodgkin Lymphoma (FL). Follicular lymphoma is the most common lymphoid malignancy in Europe and the United States. Typically it is an indolent, low grade disease consisting of an accumulation of small, resting B cells. Although the initial response to chemotherapy is good, relapses are inevitable and the disease transforms to a more aggressive histological type and develops drug resistance (Aisenberg, 1995; Johnson et al., 1995).

In over 90% of follicular lymphoma patients, a t(14;18) translocation is found, which results in the juxtaposition of the bcl-2 gene from chromosome 18q21 with the immunoglobulin heavy chain gene locus on chromosome 14q323 (Tsujimoto et al., 1985; Graninger et al., 1987). As a consequence, the bcl-2 gene comes under the influence of an immunoglobulin heavy chain enhancer, resulting in the overexpression of the Bcl-2 protein (Bakhshi et al., 1985; Tsujimoto et al., 1987). The tumorigenic potential of Bcl-2 is related to its capacity of interfering with physiological cell-death responses, thereby enhancing the longevity of the cell (Nuñez et al., 1990). The Bcl-2 protein blocks apoptotic stimuli such as growth factor deprivation, radiation, heat-shock, virus, and most DNA damaging agents for example, most chemotherapeutic agents (Reed, 1995; Hockenbery et al., 1990). In bcl-2-Ig-transgenic mice, a polyclonal follicular lymphoproliferation consisting of an expansion of mature B lymphocytes is initially observed (McDonnell et al., 1989). Subsequently, monoclonal high grade large immunoblastic type lymphomas develop and about 50% of them present rearrangement of C-MYC. This suggests that a second genetic alteration is necessary for the development and progression of malignant lymphoma (McDonnell and Korsmeyer, 1991).

An expanding family of Bcl-2-related proteins have been identified and include Bax, Bcl-$X_L$, Bcl-$X_S$, Bad, Bak, Mcl-1, A-1, and several open reading frames of DNA viruses (Oltvai et al., 1993; Boise et al., 1993; Yang et al., 1995; Chittenden et al., 1995; Kiefer et al., 1995; Kozopas et al., 1993; Lin et al., 1993; Pearson et al., 1987; Neilan et al., 1993). Membership in the Bcl-2 family of proteins is principally defined by homology within the BH1 and BH2 domains, which help regulate dimerization between the members (Sato et al., 1994). Bax, which shares 21% amino-acid identity with Bcl-2, can bind to Bcl-2 protein and neutralize its ability to block cell death. Thus, the ratio of Bcl-2 to Bax is thought to determine the cell's susceptibility to death following an apoptotic stimulus (Oltvai et al., 1993; Yin et al., 1994). U.S. Pat. No. 5,837,838 to Reed et al., 1998c, provides methods for identifying agents that can modulate the binding of a Bax-inhibitor protein to a member of the Bcl-2 family of proteins.

Phosphodiester antisense oligodeoxynucleotides complementary to specific sequences of the translation-initiation site of Bcl-2 mRNA are able to inhibit the production of the Bcl-2 protein and thereby inhibit the growth of t(14;18) translocation bearing cells (Kitada et al., 1993). However, therapeutic use of phosphodiester oligonucleotides is hampered by their low cellular uptake and their rapid degradation by nucleases and other serum or cellular components. Phosphorothioate oligonucleotides, which are resistant to nuclease degradation, were found to inhibit follicular lymphoma cell growth at concentrations 10 times lower than phosphodiester oligonucleotides (Reed et al., 1990a; Reed et al., 1990b; Cotter et al., 1994). However, this approach suffers from low cellular uptake of the oligonucleotides. For example, Reed et al., (1990a) and Reed et al., (1998a), had to use concentrations of greater than 25 µM of phosphorothioates to achieve 50% growth inhibitions of human leukemic cell-lines Su-Dhl-4, RS11846, 679 and JURKAT and in human PBL (peripheral blood lymphocytes).

Incorporation of oligonucleotides into liposomes has increased their uptake into leukemic cells (Akhtar et al., 1991; Tari et al., 1994). The use of cationic lipids by Reed et al., to deliver phosphorothioate antisense oligonucleotides allowed them to reduce the concentration of oligonucleotides to 0.075 to 0.3 µM and still induce growth inhibition in Su-Dhl-4 cells.

In a related invention, disclosed in U.S. patent application Ser. No. 09/112,869, filed Jul. 9, 1998, the present inventors describe various liposomal compositions of antisense oligonucleotides and methods of making these compositions. The application also describes the use of these liposomal compositions to deliver antisense oligonucleotides to tumor cells and methods for inhibiting the growth of tumor cells.

U.S. Pat. No. 5,734,033 (Reed et. al., 1998a), reports the use of antisense oligonucleotide sequences derived from regions of the translation-initiation site of the bcl-2 gene which are 10 bases or greater in length for the inhibition of growth of leukemic cells and human PBL cells. However, there are no examples demonstrating the synthesis and use of antisense oligonucleotides shorter than 15-mers. Also, both the phosphorothioate and the phosphodiester antisense oligonucleotides were required at concentrations greater than 25 µM for the inhibition of about 50% of cell growth in the human leukemic cell-lines RS11846, 679 and JURKAT and in human PBL (peripheral blood lymphocytes).

Related U.S. Pat. No. 5,831,066 to Reed (1998b), proposes that antisense oligomers of from 2 to 200 nucleotides in length will bind to a human bcl-2 mRNA at the translation initiation site and reduce bcl-2 expression in tumor cells. However, again, there is no disclosure reciting the synthesis and successful use of antisense oligonucleotides shorter than 15 mers.

There is, therefore, a great need for better compositions for the treatment of Bcl-2 associated diseases such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

SUMMARY OF THE INVENTION

The present invention overcomes these and other deficiencies in the art and demonstrates the use of very short bcl-2 antisense oligonucleotides in lipid formulations, ranging from 7 bases to 9 bases, that induce growth inhibition in human leukemic cells. This is an unexpected result in light of U.S. Pat. No. 5,734,033, to Reed et al., 1998a, which reports a lower limit of 10 bases for the antisense oligonucleotides. It is well known to one of skill in the art, that while all or part of a gene sequence may be employed in the context of antisense construction, statistically, any sequence of at least 17 bases long should occur only once in the human genome and, therefore, be essential to specify a unique target sequence. In light of this knowledge, it is surprising that in the present invention, short oligonucleotides, defined herein as oligonucleotides of 9 or less bases in length, such as oligonucleotides 9 bases, 8 bases and/or 7 bases in length, have been used with success as specific antisense molecules towards bcl-2. In contrast to conventional wisdom, which dictates that both binding affinity and sequence specificity of an oligonucleotide for its complementary target, increase with increasing length, the inventors have demonstrated the successful use of short oligonucleotides.

Additionally, in the present invention, the concentrations of the short antisense oligonucleotides in lipid formulations, for example, the short oligonucleotides represented by SEQ ID NO: 2, SEQ ID NO: 3, SEQ ID NO: 4, and SEQ ID NO: 5, used to achieve 50% growth inhibition in leukemic cells are low and range from about 3 to 12 µM. This result is also true for the oligonucleotides of this invention which are longer than 9 bases. Specifically, two 11 base long oligonucleotides represented by SEQ ID NO: 6 and SEQ ID NO: 7; and two 15 base long oligonucleotides represented by SEQ ID NO: 8, and SEQ ID NO: 9 are very efficient in controlling the growth of a human leukemia cell line and are required at a concentration of only 3 to 4 µM to achieve 50% growth inhibition.

The findings of Reed et. al., 1998a, which reports the use of bcl-2 antisense phosphorothioate oligonucleotides of 10 bases or greater, which are not liposomal formulations, require concentrations greater than 25 µM for the inhibition of 50% of cell growth in some human leukemic cell-lines and in human PBL (peripheral blood lymphocytes). Furthermore, in Reed et al., 1998b, concentrations of greater than 60 µM are required for about 50% growth inhibition of leukemic cells.

Thus, in one embodiment, the present invention provides a composition comprising a short antisense oligonucleotide, of from seven bases to nine bases in length, that is complementary to a Bcl-2 oligonucleotide, and a lipid component. In a further embodiment, the oligonucleotide includes a region that is complementary to a portion of, or overlaps with a portion of, the translation initiation site of Bcl-2 mRNA. In certain specific embodiments, the oligonucleotide will include the sequence SEQ ID NO: 2, SEQ ID NO: 3, SEQ ID NO: 4, or SEQ ID NO: 5.

In another aspect of the invention, the oligonucleotide may be greater than nine bases in length. In a specific embodiment of this aspect, the oligonucleotide is 11 or 15 bases long and has the sequence corresponding to SEQ ID NO: 6, SEQ ID NO: 7, SEQ ID NO: 8, or SEQ ID NO: 9.

In one aspect, the lipid component of the composition comprises liposomes. In another aspect the short antisense oligonucleotide is encapsulated in liposomes, interspersed within the lipid bilayer of a liposome, attached to a liposome via a linking molecule that is associated with both the liposome and the oligonucleotide, complexed with a lipid, dispersed in a solution containing a lipid, mixed with a lipid, combined with a lipid, contained as a suspension in a lipid, contained or complexed with a micelle, or otherwise associated with a lipid.

The term "lipids" as used in this specification and the claims denotes any form of both naturally occurring and synthetic lipids or liposomes. They are fatty substances and are well-known to those of skill in the art. The lipids of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

In a preferred embodiment, the lipid material is comprised of a neutrally charged lipid. A neutrally charged lipid can comprise a lipid without a charge, a substantially uncharged lipid or a lipid mixture with equal number of positive and negative charges.

In one aspect, the lipid component of the composition comprises a neutral lipid. In another aspect, the lipid material consists essentially of neutral lipids which is further defined as a lipid composition containing at least 70% of lipids without a charge. In other preferred aspect, the lipid material may contain at least 80% to 90% of lipids without a charge. In yet other preferred aspects, the lipid material may comprise about 90%, 95%, 96%, 97%, 98%, 99% or 100% lipids without a charge.

The preferred lipid in the present invention is comprised of dioleoylphosphatidylcholine. However, other lipids such as phosphatidylcholines, phosphatidylglycerols, and phosphatidylethanolamines may also be employed.

In other aspects the lipid component comprises a substantially uncharged lipid. A substantially uncharged lipid is described herein as a lipid composition that is substantially free of anionic and cationic phospholipids and cholesterol. In yet other aspects the lipid component comprises a mixture of lipids to provide a substantially uncharged lipid. Thus, the lipid mixture may comprise negatively and positively charged lipids.

Compositions of the present invention also include compositions wherein liposomes are formed from a lipid. In some cases, it may be useful to have a composition in which the short oligonucleotide is encapsulated in the liposome. Phospholipids are preferably used for preparing the liposomes according to the present invention and can carry a net positive charge; a net negative charge; or are neutral. The liposomes can be made of one or more phospholipids. Suitable phospholipids include phosphatidyl cholines and others that are well known to those of skill in the art. Diacetyl phosphate can be employed to confer a negative charge on the liposomes, and stearylamine can be used to confer a positive charge on the liposomes.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Thus, one embodiment of the present invention, comprises a liposomal composition of antisense oligonucleotides. The composition includes (a) a liposome which consists essentially of lipids, and (b) a short antisense oligonucleotide, 7 bases to 9 bases in length, that is entrapped in the liposome. In an alternate embodiment, the antisense oligonucleotide may be longer than 9 bases in length and can be 11 bases long and have the sequences represented in SEQ. ID. NO: 6 and SEQ. ID. NO: 7; or can be 15 bases long and have the sequences represented in SEQ. ID. NO: 8, or SEQ. ID. NO: 9.

The antisense oligonucleotide of the invention is preferably composed of a nuclease resistant backbone. Thus, in a preferred embodiment, short antisense p-ethoxy oligonucleotides are contemplated. In alternate embodiments, short antisense phosphorothioate oligonucleotides are contemplated. Furthermore, it is envisioned that any short antisense oligonucleotide that is composed of a nuclease resistant backbone may be used. In yet other embodiments, the use of phosphodiester oligonucleotides are also contemplated.

When the antisense oligonucleotide is a p-ethoxy oligonucleotide, the preferred molar ratio of phospholipid to oligo is between about 5:1 and about 100:1. In a preferred embodiment, for the p-ethoxy oligonucleotides, the molar ratio of phospholipid to oligo is 20:1. A preferred embodiment comprises a) p-ethoxy oligonucleotides and b) the phospholipid dioleoylphosphatidylcholine in a molar ratio of 20:1. When the antisense oligonucleotide is a phosphorothioate oligonucleotide, the preferred molar ratio of phospholipid to oligo is between about 10:1 and about 50:1. When the antisense oligonucleotide is a phosphodiester oligonucleotide, the preferred molar ratio of phospholipid to oligo is less than about 3,000:1.

The short antisense oligonucleotide of the composition may comprises the sequence 5'GCCATCC3' (SEQ ID NO:2), 5'TCCTTCC3' (SEQ ID NO:3), 5'CGCCATCCT3' (SEQ ID NO:4), or 5'ATCCTTCCC3' (SEQ ID NO:5). Alternatively, the antisense oligonucleotide of the composition may be a 11 base pair sequence which is selected from the group comprising 5'GCGCCATCCTT3' (SEQ ID NO:6) and 5'GCCATCCTTCC3' (SEQ ID NO:7). Yet alternatively, the antisense oligonucleotide of the composition may be a 15 base pair sequence which is selected from the group comprising 5'GTGCGCCATCCTTCC3' (SEQ ID NO:8) and 5'TGCGCCATCCTTCCC3' (SEQ ID NO:9).

In yet another embodiment, there is provided a composition comprising an expression construct that encodes a short oligonucleotide that is complementary to a Bcl-2 oligonucleotide, wherein the antisense oligonucleotide includes a region complementary to a region of the translation initiation site of Bcl-2 mRNA and wherein the short oligonucleotide is under the control of a promoter that is active in eukaryotic cells. In a specific embodiment, the short oligonucleotide can comprise oligonucleotides of the sequences represented in SEQ. ID. NO: 2, SEQ. ID. NO: 3, SEQ. ID. NO: 4, and SEQ. ID. NO: 5.

An alternative embodiment provides a composition comprising an expression construct that encodes a first oligonucleotide, that is either 11 bases long or 15 bases long, wherein the antisense oligonucleotide includes a region complementary to, or a region that overlaps with a region of the translation initiation site of Bcl-2 mRNA and wherein said first oligonucleotide is under the control of a promoter that is active in eukaryotic cells. In a specific embodiment of the above, the first oligonucleotide can comprise oligonucleotides of the sequences represented in SEQ. ID. NO: 6, SEQ. ID. NO: 7, SEQ. ID. NO: 8, and SEQ. ID. NO: 9.

This invention may be employed to treat a Bcl-2-associated disease. In one embodiment, the invention provides a method for inhibiting a Bcl-2-associated disease comprising: a) obtaining an antisense oligonucleotide having a length of from 7 to 15 bases in length that includes a region complementary to a Bcl-2 oligonucleotide; b) mixing the antisense oligonucleotide with a lipid to form an oligonucleotide-lipid mixture; and c) administering said mixture to a cell. In a specific embodiment, the antisense oligonucleotide is a short oligonucleotide, having a length of from 7 to 9 bases and having the sequence SEQ ID NO: 2, SEQ ID NO: 3, SEQ ID NO: 4, and SEQ ID NO: 5. In other specific embodiments, the antisense oligonucleotide is a 11 base long sequence represented by SEQ. ID. NO: 6 and SEQ. ID. NO: 7; and/or is a 15 base long sequence represented by SEQ. ID. NO: 8 and SEQ. ID. NO: 9. These antisense oligonucleotide or portions thereof may be complementary to a region or a portion of the translation initiation site of Bcl-2 mRNA.

The invention also comprises a method for inhibiting the proliferation of a cancer cell comprising contacting said cancer cell with a composition comprising at least one short oligonucleotide, 7 bases to 9 bases in length, that is complementary to a portion of a Bcl-2 oligonucleotide. In certain specific embodiments, the short oligonucleotide may be an oligonucleotide having the sequence SEQ ID NO: 2, SEQ ID NO: 3, SEQ ID NO: 4, and SEQ ID NO: 5. In yet another specific embodiment, the invention comprises a method for inhibiting the proliferation of a cancer cell comprising contacting said cancer cell with a composition comprising at least one oligonucleotide, that is 11 bases in length or 15 bases in length, wherein the oligonucleotide has the sequence represented by SEQ ID NO: 6, SEQ ID NO: 7, SEQ ID NO: 8, and SEQ ID NO: 9.

These methods may be applied advantageously to a cancer cell where the cancer cell is a lymphoma cell, a follicular lymphoma cell, a breast cancer cell, a prostate cancer cell, a liver cancer cell, a pancreatic cancer cell, a lung cancer cell, a brain cancer cell, an ovarian cancer cell, a testicular cancer cell, a skin cancer cell, a leukemia cell, a head and neck cancer cell, an esophageal cancer cell, a stomach cancer cell, a kidney cancer cell, a colon cancer cell and a rectal cancer cell.

The composition may further comprise a lipid which is associated with the oligonucleotide, for example, an oligonucleotide encapsulated in a liposome. In a specific embodiment, the contacting takes place in a patient. The patient may be a human. The composition may advantageously be delivered to a human patient in a volume of 0.50-10.0 ml per dose or in an amount of 5-30 mg oligonucleotide per $m^2$. In a particular regimen, the composition is administered 3 times per week for 8 weeks.

"A" or "an" is defined herein to mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

A. The Present Invention

Figure 1A:
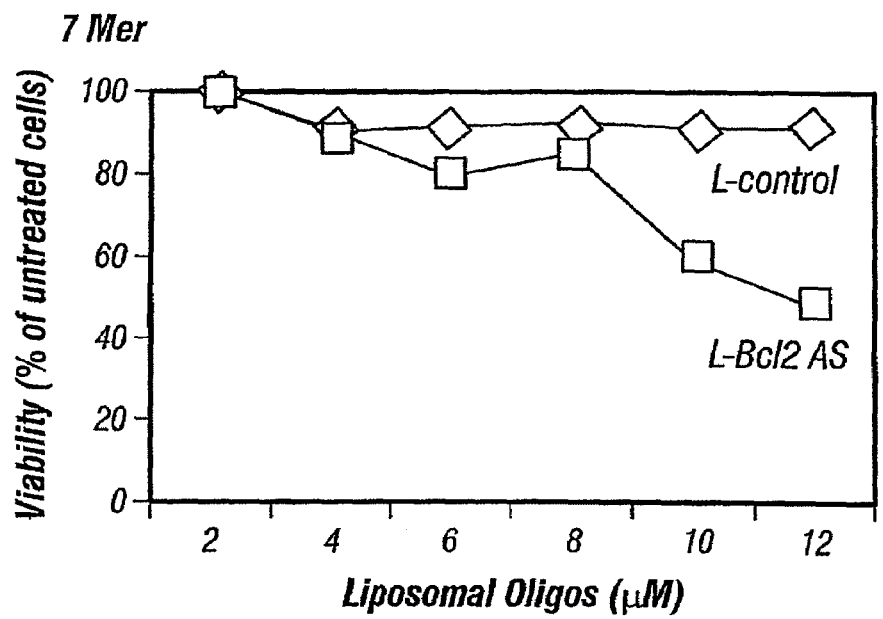
FIG. 1A-1H. Effects of Antisense Oligonucleotide Length on Cell Viability.
Figure 1B:
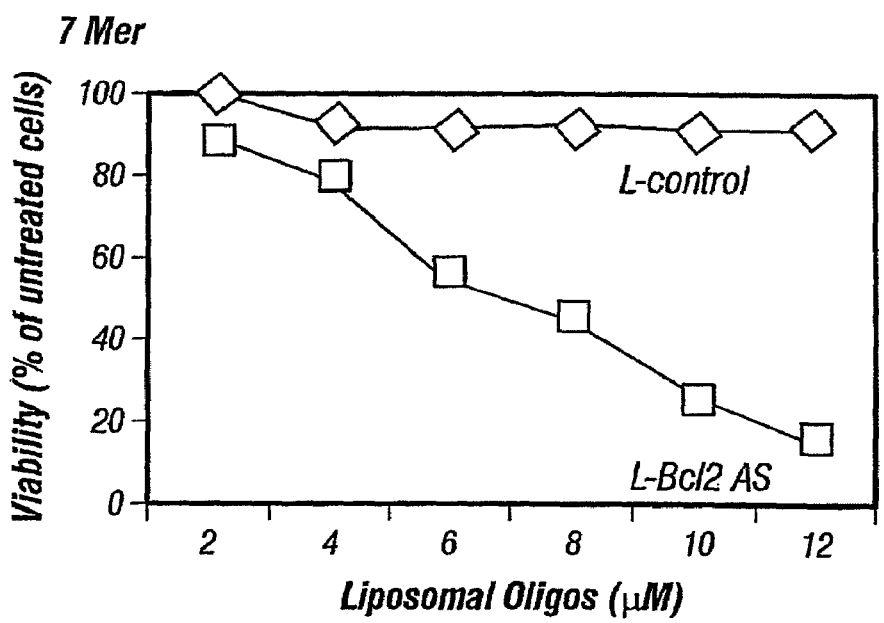
Figure 1C:
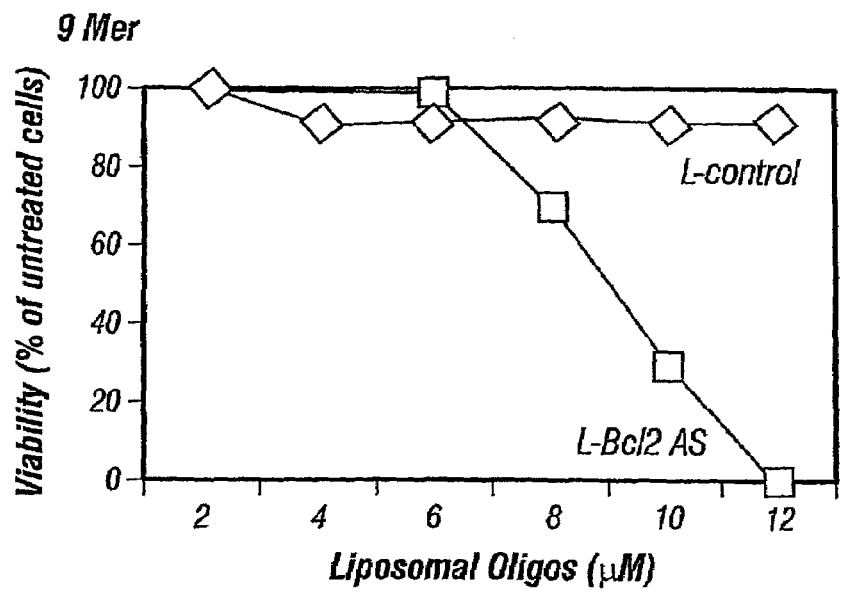
Figure 1D:
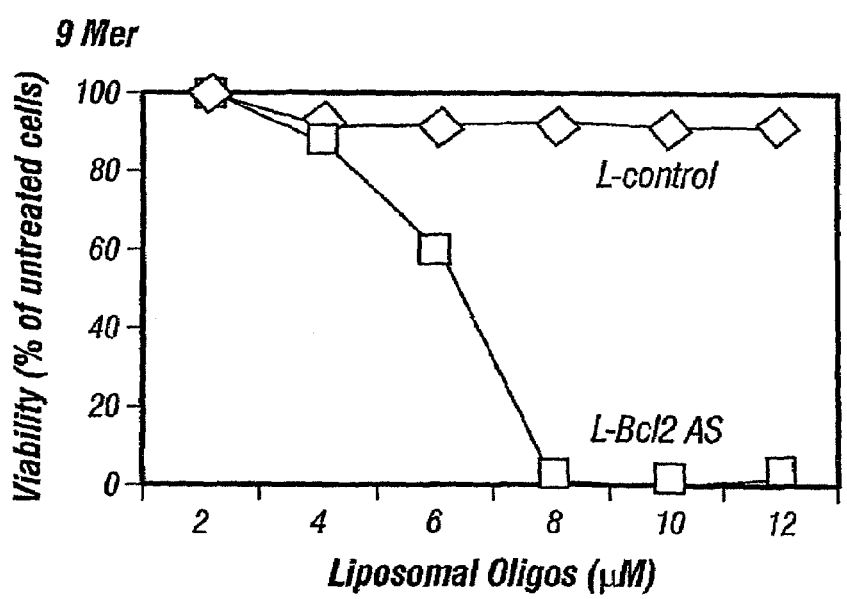
Figure 1E:
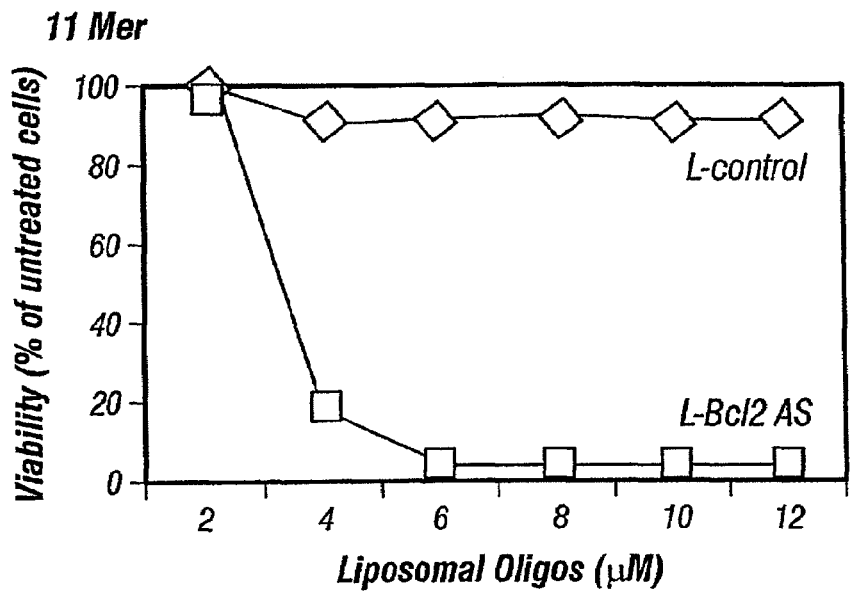
Figure 1F:
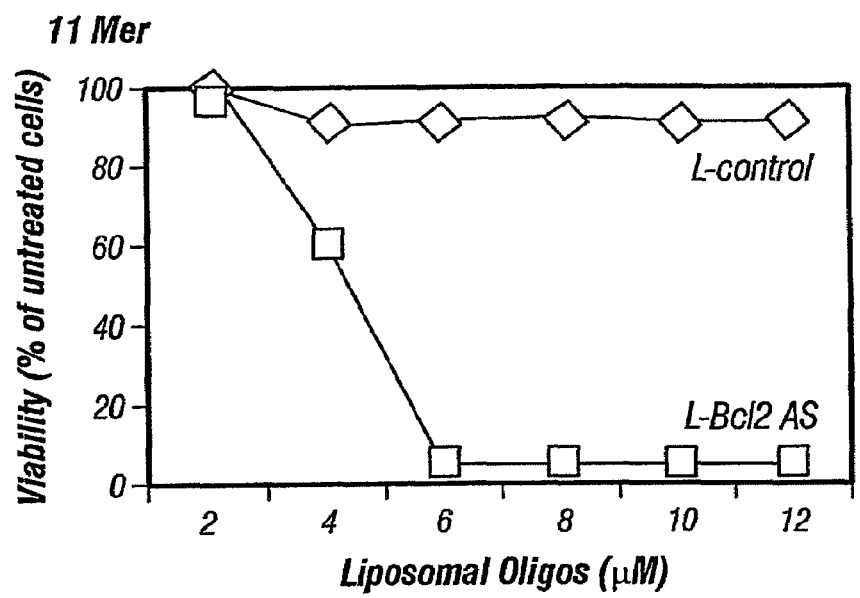
Figure 1G:
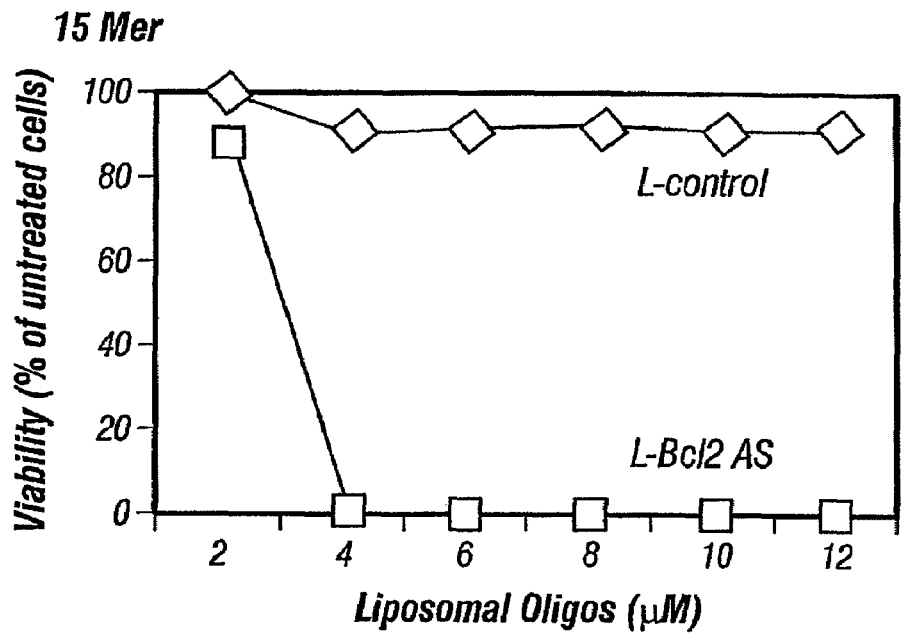
Figure 1H:
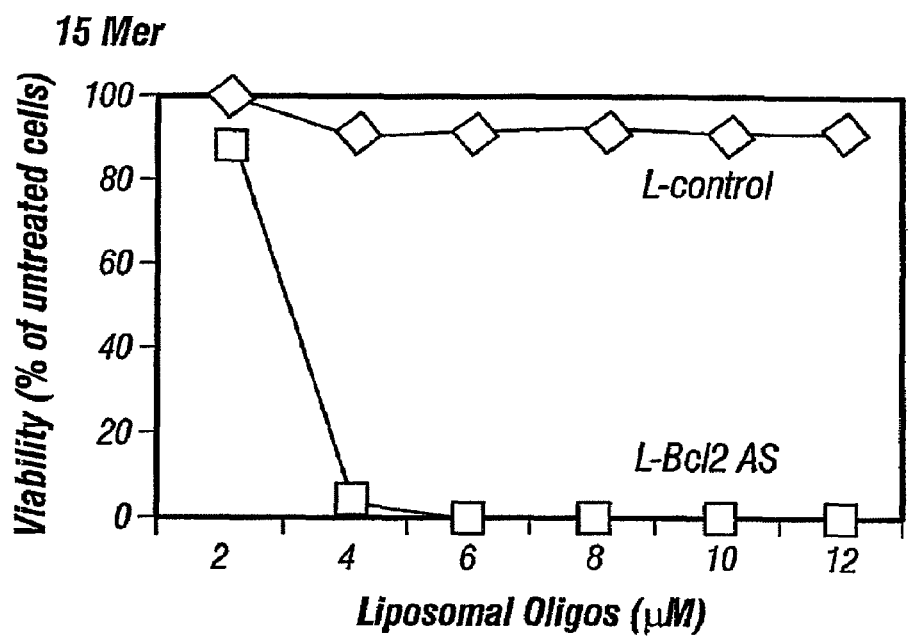

Bcl-2 is an oncogene with tumorigenic potential due to its capacity to block programmed cell death. The present invention relates to short antisense oligonucleotides directed to portions of the bcl-2 gene and their use in the treatment of Bcl-2 related diseases. In one embodiment, the present invention employs short antisense oligodeoxynucleotides, that are 9 bases or less, that are associated with a lipid, to inhibit the production of Bcl-2 so that tumor cells can regain the capacity to enter programmed cell death. In another embodiment of the invention, the use of specific antisense oligonucleotides directed to portions of the translational-initiation region of bcl-2 are disclosed. In this aspect, two 11-mers, bearing SEQ. ID NO: 6, SEQ. ID. NO: 7; and two 15-mers, bearing SEQ ID. NO: 8 and SEQ ID. NO: 9 are shown to inhibit the production of Bcl-2 in CJ cells (which are cells of a transformed follicular lymphoma derived cell-line) and cause the inhibition of cell growth. The present invention may therefore be used to treat hematologic malignancies, both leukemias and lymphomas, including follicular and nonfollicular lymphomas, chronic lymphocytic leukemia, and plasma cell dyscrasias; solid tumors like those associated with breast, prostate, colon, liver, pancreas, lungs, brain, ovary, testis, skin, head and neck, esophageal, stomach, kidney and rectal cancers; and immune disorders, which are associated with Bcl-2 expression.

A specific type of cancer that may be treated by the methods of the present invention is follicular lymphoma. Over 90% of follicular lymphoma patients have a t(14;18) translocation which results in the translocation of the bcl-2 gene from its normal location in chromosome 18 to the immunoglobulin heavy chain gene locus on chromosome 14. In consequence, the bcl-2 gene is under the influence of the immunoglobulin heavy chain enhancer, and the Bcl-2 protein is overexpressed. Since bcl-2 is an oncogene with tumorigenic potential due to its capacity to block programmed cell death, a potential therapy for these follicular lymphomas is to inhibit the production of the Bcl-2 protein. The present invention is unexpected and novel as it uses short antisense oligonucleotides associated with lipids that are entirely or in-part complementary to portions of the translation initiation site of the Bcl-2 mRNA to inhibit the production of Bcl-2 protein.

It is contemplated that the use of these small antisense molecules, either alone or in conjunction with other antisense molecules, will provide an effective treatment for follicular lymphoma and other cancers. For example, the present invention teaches that treatment with short bcl-2 antisense oligonucleotides, of from 7 bases to 9 bases, inhibits the growth of CJ cells that are known to overexpress the Bcl-2 protein. In some embodiments, the oligo- or polynucleotides themselves, or expression vectors encoding them, may be employed. The preferred method for delivering these nucleic acids is via liposomes. The invention, in its various embodiments, is described in greater detail, below.

B. Oligonucleotides

The term "antisense" is intended to refer to oligonucleotide or polynucleotide molecules complementary to a portion of a Bcl-2 RNA, or the DNA's corresponding thereto. "Complementary" oligonucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with oligonucleotides leads to triple-helix formation; targeting RNA will lead to double-helix formation. Antisense oligonucleotides, when introduced into a target cell, specifically bind to their target oligonucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mM (10 mM Na$^+$; 150 mM K$^+$). The intracellular concentration of divalent cation is approximately 20 mM (18 mM Mg$^{++}$; 2 mM Ca$^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to portions of the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean oligonucleotides that are substantially complementary over their entire length and have very few base mismatches. For example, sequences of seven bases in length may be termed complementary when they have a complementary nucleotide for five or six positions out of seven. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The oligonucleotides according to the present invention may encode a bcl-2 gene or a portion of that gene that is sufficient to effect antisense inhibition of protein expression. The oligonucleotides may be derived from genomic DNA, i.e., cloned directly from the genome of a particular organism. In other embodiments, however, the oligonucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense oligonucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized oligonucleotide may provide more convenient restriction sites for the remaining portion of the construct and, therefore, would be used for the rest of the sequence.

The DNA and protein sequences for bcl-2 are published in literature by Tsujimoto and Croce (1986) (SEQ ID NO:11, SEQ ID NO:12, SEQ ID NO:13, & SEQ ID NO:14) which is incorporated herein by reference. It is contemplated that natural variants of Bcl-2 exist that have different sequences than those disclosed herein. Thus, the present invention is not limited to use of the provided oligonucleotide sequence for Bcl-2 but, rather, includes use of any naturally-occurring variants. Depending on the particular sequence of such variants, they may provide additional advantages in terms of target selectivity, i.e., avoid unwanted antisense inhibition of related transcripts. The present invention also encompasses chemically synthesized mutants of these sequences.

As stated above, although the antisense sequences may be full length genomic or cDNA copies, or large fragments thereof, they also may be shorter fragments, or "short oligonucleotides," defined herein as oligonucleotides of from 7 bases to 9 bases. Although shorter oligomers, 7 bases to 9 bases, are easier to make and increase in vivo accessibility, numerous other factors are also involved in determining the specificity of base-pairing. For example, both binding affinity and sequence specificity of an oligonucleotide to its complementary target increase with increasing length. It is contemplated that oligonucleotides of 7, 8, or 9 bases may be used.

In certain embodiments oligonucleotide sequences, longer than 9 bases, for example, of 11 bases and 15 bases bearing SEQ ID NO: 6, SEQ ID. NO: 7, SEQ ID. NO: 8 and SEQ ID. NO: 9 may be used. Other such specific oligonucleotide sequences, longer than 9 bases, for example, 10, 11, 12, 13, 14, 15, 16, 17, 18, 19 or 20 bases may also be used.

In the present invention any antisense oligonucleotide that is composed of a nuclease resistant backbone and has a favorable binding temperature to allow efficient binding to a target may be used. Thus, a preferred antisense oligonucleotide of this embodiment is a p-ethoxy oligonucleotide. However, phosphodiester oligonucleotides and/or phosphorothioate oligonucleotides are also contemplated. It is also envisioned that any other oligonucleotides with nuclease resistant backbones and favorable binding temperatures may be used.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense oligonucleotide. Ribozyme sequences also may be modified in much the same way as described for antisense oligonucleotide. For example, one could incorporate non-Watson-Crick bases, or make mixed RNA/DNA oligonucleotides, or modify the phosphodiester backbone.

Alternatively, the antisense oligo- or polynucleotides of the present invention may be provided as mRNA via transcription from expression constructs that carry nucleic acids encoding the oligonucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 by of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 by upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 by apart before activity begins to decline. Depending on the promoter, it appears that individual elements can function either cooperatively or independently to activate transcription.

The particular promoter that is employed to control the expression of a nucleic acid encoding the antisense oligonucleotides of this invention is not believed to be important, so long as it is capable of expressing the antisense oligonucleotide in the targeted cell. Thus, where a human cell is targeted, it is preferable to position the nucleic acid coding an antisense oligonucleotide described in this invention adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various antisense oligonucleotides described and contemplated in this invention. The use of other viral or mammalian cellular or bacterial phage promoters are well-known to one of skill in the art and the present invention contemplates the use of these promoters as well, provided that the levels of expression of the antisense oligonucleotides are sufficient for the given purpose.

By employing a promoter with well-known properties, the level and pattern of expression of an antisense oligonucleotide can be optimized. Further, selection of a promoter that is regulated in response to specific physiologic signals can permit inducible expression of an antisense oligonucleotide described herein. For example, a nucleic acid under control of the human PAI-1 promoter results in expression inducible by tumor necrosis factor. Tables 1 and 2 list several elements/promoters which may be employed, in the context of the present invention, to regulate the expression of antisense constructs. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding an antisense oligonucleotide described in this invention in an expression construct (Table 1 and Table 2). Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |

TABLE 1-continued

| PROMOTER |
| --- |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
| --- | --- |
| MT II | Phorbol Ester (TPA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester (TPA) |
| Tumor Necrosis Factor | PHA |
| Thyroid Stimulating Hormone α Gene | Thyroid Hormone |

In certain embodiments of this invention, the delivery of a nucleic acid to a cell may be identified in vitro or in vivo by including a marker in the expression construct. The marker would result in an identifiable change to the transfected cell permitting easy identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. Examples include the SV40, globin or adenovirus polyadenylation signals. Also contemplated as an element of the expression cassette is a terminator. These elements can serve to enhance message levels and to minimize read through from the cassette into other sequences.

C. Hybridization

Hybridization is a process by which two complementary nucleic acid strands, such as DNA and DNA, RNA and DNA or RNA and RNA, recognize and bind to each other and form a double stranded structure. Intracellular hybridization is the basis of antisense therapy, which involves the administration/ delivery of an antisense nucleic acid to a cell where the antisense molecule finds its complementary target-nucleic acid, which may be either DNA or RNA, and hybridizes to it thereby preventing further transcription or translation of the target-nucleic acid.

The technique of hybridization is also employed to identify nucleic acid products by the nature of the complementarity of a target gene to a hybridization probe. Accordingly, nucleotide sequences may be selected for their ability to selectively form duplex molecules with complementary stretches of genes or RNAs. Depending on the application envisioned, varying conditions of hybridization can be used to achieve varying degrees of selectivity of probe towards target sequence.

For applications requiring high selectivity, one typically will employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, it is appreciated that lower stringency conditions are required. Under these conditions, hybridization may occur even though the sequences of probe/primer and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C.

The selected conditions will depend on the particular circumstances based on the particular criteria required (depending, for example, on the G+C content, type of target nucleic acid, source of nucleic acid, size of hybridization probe, etc.). Following washing of the hybridized surface to remove nonspecifically bound probe/primer molecules, hybridization is detected, or even quantified, by means of the label.

In general, it is envisioned that hybridization of the antisense oligonucleotides of the present invention to the translation initiation site of bcl-2 mRNA will be the basis of the antisense-gene therapy aimed at Bcl-2 mediated diseases. Intracellular hybridization will prevent the transcription of bcl-2 mRNA and thereby decrease the Bcl-2 protein content in the cell to which the antisense oligonucleotide is administered to. This will cause the cell to undergo normal apoptosis due to the reduction of cellular Bcl-2 concentration.

D. Lipid Formulations

In a preferred embodiment of the invention, the antisense oligonucleotides and expression vectors may be associated with a lipid. An oligonucleotide associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/oligonucleotide associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine.

Phospholipids may be used for preparing the liposomes according to the present invention and can carry a net positive charge, a net negative charge or are neutral. Diacetyl phosphate can be employed to confer a negative charge on the liposomes, and stearylamine can be used to confer a positive charge on the liposomes. The liposomes can be made of one or more phospholipids.

In a preferred embodiment, the lipid material is comprised of a neutrally charged lipid. A neutrally charged lipid can comprise a lipid without a charge, a substantially uncharged lipid or a lipid mixture with equal number of positive and negative charges.

In one aspect, the lipid component of the composition comprises a neutral lipid. In another aspect, the lipid material consists essentially of neutral lipids which is further defined as a lipid composition containing at least 70% of lipids without a charge. In other preferred aspects, the lipid material may contain at least 80% to 90% of lipids without a charge. In yet other preferred aspects, the lipid material may comprise about 90%, 95%, 96%, 97%, 98%, 99% or 100% lipids without a charge.

In specific aspects, the neutral lipid comprises a phosphatidylcholine, a phosphatidylglycerol, or a phosphatidylethanolamine. In a preferred aspect, the phosphatidylcholine comprises dioleoylphosphatidylcholine.

In other aspects the lipid component comprises a substantially uncharged lipid. A substantially uncharged lipid is described herein as a lipid composition that is substantially free of anionic and cationic phospholipids and cholesterol. In yet other aspects the lipid component comprises a mixture of lipids to provide a substantially uncharged lipid. Thus, the lipid mixture may comprise negatively and positively charged lipids.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. Such expression vectors have been successfully employed in transfer and expression of an oligonucleotide in vitro and in vivo and thus are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. A novel and preferred method of the invention describes the preparation of liposomes and is described below and in the Examples section. Briefly, p-Ethoxy-oligonucleotides (also referred to as pE oligos) are dissolved in DMSO and the phospholipids (Avanti Polar Lipids, Alabaster, Ala.), such as for example the preferred neutral phospholipid dioleoylphosphatidylcholine (DOPC), is dissolved in tert-butanol. The lipid is then mixed with the antisense oligonucleotides. In the case of DOPC, the ratio of the lipid to the antisense oligos is 20:1. Tween 20 is added to the lipid:oligo mixture such that Tween 20 is 5% of the combined weight of the lipid and oligo. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used upto three months. When required the lyophilized liposomes are reconstituted in 0.9% saline. The average diameter of the particles obtained using Tween 20 for encapsulating the lipid with the oligo is 0.7-1.0 µm in diameter.

Alternatively liposomes can be prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287-341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

P-ethoxy oligonucleotides, nucleases resistant analogues of phosphodiesters, are preferred because they are stable in serum. Neutral lipids are also preferred and specifically the lipid dioleoylphosphatidylchoine is preferred. However other lipids such as other phosphatidylcholines, phosphatidylglycerols, and phosphatidylethanolamines may also be useful. In a new and preferred method described herein, the nuclease-resistant oligonucleotides and lipids are dissolved in DMSO and t-butanol respectively. The lipid is then mixed with the oligonucleotides in a ratio of between about 5:1 to about 100:1, and preferably in a ratio of 20:1. The preferred lipid: oligonucleotide ratio for p-ethoxy oligonucleotides and the lipid dioleoylphosphatidylchoine is 20:1. Tween 20 is then added to the mixture to obtain the liposomes. Excess t-butanol is added and the mixture is vortexed, frozen in a acetone/dry-ice bath, and then lyophilized overnight. The preparation is stored at −20° C. and may be used within one month of preparation. When required for use the lyophilized liposomal antisense oligonucleotides are reconstituted in 0.9% saline.

In an alternative embodiment, nuclease-resistant oligonucleotides are mixed with lipids in the presence of excess t-butanol. The mixture is vortexed before being frozen in an acetone/dry ice bath. The frozen mixture is then lyophilized and hydrated with Hepes-buffered saline (1 mM Hepes, 10 mM NaCl, pH 7.5) overnight, and then the liposomes are sonicated in a bath type sonicator for 10 to 15 min. The size of the liposomal-oligonucleotides typically ranges between 200-300 nm in diameter as determined by the submicron particle sizer autodilute model 370 (Nicomp, Santa Barbara, Calif.).

A pharmaceutical composition comprising the liposomes will usually include a sterile, pharmaceutically acceptable carrier or diluent, such as water or saline solution.

E. Alternative Delivery Systems

Retroviruses The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a Bcl-2 antisense construct as described in this invention is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing an inserted DNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Adenoviruses Human adenoviruses are double-stranded DNA tumor viruses with genome sizes of approximate 36 kB. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

A small portion of the viral genome appears to be required in cis adenovirus-derived vectors when used in connection with cell lines such as 293 cells. Ad5-transformed human embryonic kidney cell lines (Graham, et al., 1977) have been developed to provide the essential viral proteins in trans.

Particular advantages of an adenovirus system for expressing and delivering the antisense oligonucleotides of this invention include (i) the structural stability of recombinant adenoviruses; (ii) the safety of adenoviral administration to humans; and (iii) lack of any known association of adenoviral infection with cancer or malignancies; (iv) the ability to obtain high titers of the recombinant virus; and (v) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. Surprisingly persistent expression of transgenes following adenoviral infection has also been reported.

Other Viral Vectors as Expression Constructs Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedman et al., 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Methods Several non-viral methods for the transfer of expression vectors into cultured mammalian cells also are contemplated in the present invention. These include calcium phosphate precipitation (Graham and van der Eb, 1973; Chen and Okayama, 1987; Rippe et al., 1990); DEAE-dextran (Gopal, 1985); electroporation (Tur-Kaspa et al., 1986; Potter et al., 1984); direct microinjection (Harland and Weintraub, 1985); DNA-loaded liposomes (Nicolau and Sene, 1982; Fraley et al., 1979); lipofectamine-DNA complexes; cell sonication (Fecheimer et al., 1987); gene bombardment using high velocity microprojectiles (Yang et al., 1990); polycations; and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an Bcl-2 antisense oligonucleotide construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a Bcl-2 antisense oligonucleotide as described in this invention may be delivered via this method.

F. Pharmaceutical Compositions and Routes of Administration

Where clinical application of liposomes containing antisense poly- or oligonucleotides is undertaken, it will be necessary to prepare the liposome complex as a pharmaceutical composition appropriate for the intended application. This is also true for expression vectors encoding the short antisense poly- or oligonucleotides of the invention. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense oligonucleotide encapsulated in a liposome as discussed above, further dispersed in pharmaceutically acceptable carrier or aqueous medium. They may also comprise aqueous compositions of the vectors encoding antisense poly- or oligonucleotides of the invention in one of the vector delivery systems described above. Such compositions also are referred to as inocula. The phrases "pharmaceutically" or "pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycol's, mixtures thereof and in oils. Under ordinary conditions of storage and use, these preparations contain a preservative to prevent the growth of microorganisms.

The therapeutic compositions of the present invention are advantageously administered in the form of indictable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc.

Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for the treatment of skin cancers, to prevent chemotherapy-induced alopecia or other dermal hyperproliferative disorder. Alternatively, administration may be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting the dose include the physical and clinical state of the patient, the route of administration, the intended goal of treatment (alleviation of symptoms versus cure) and the potency, stability and toxicity of the particular therapeutic substance. For the instant application, it is envisioned that the amount of unit dose will range from about 5-30 mg of oligonucleotide.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Oligonucleotides

Antisense Oligonucleotides

Nuclease-resistant p-ethoxy oligonucleotides, non-ionic phosphodiester analogs, were purchased from Oligo Therapeutics (Willsonville, Oreg.). Alternatively other oligonucleotides such as phosphodiester or phosphorothioate oligonucleotides may also be used and are commercially available. The following oligonucleotide sequences (also listed in Table 3), that corresponds to bcl-2 antisense, specific for the translation initiation site of human Bcl-2 mRNA, were synthesized and used: 5'CAGCGTGCGCCATCCTTCCC3' (SEQ ID NO:1), a 20-mer; 5'GCCATCC3' (SEQ ID NO:2) a 7-mer, 5'TCCTTCC3' (SEQ ID NO:3), another 7-mer; 5'CGCCATCCT3' (SEQ ID NO:4), a 9-mer; 5'ATCCTTCCC3' (SEQ ID NO:5), another 9-mer; 5'GCGCCATCCTT3' (SEQ ID NO:6), a 11-mer, 5'GCCATCCTTCC3' (SEQ ID NO:7), another 11-mer; 5'GTGCGCCATCCTTCC3' (SEQ ID NO:8), a 15-mer; and 5'TGCGCCATCCTTCCC3' (SEQ ID NO:9), another 15-mer. As a control, a scrambled version of bcl-2 antisense oligonucleotide, with the sequence: 5'TCGCCACTCGATCCTGCCCG3' (SEQ ID NO:10) was used.

TABLE 3

| Sequences of Various Bcl-2 Antisense Oligonucleotides | |
| --- | --- |
| SEQ. ID. No. 1 | 5'CAGCGTGCGCCATCCTTCCC3' |
| SEQ ID. NO: 2 | 5'GCCATCC3' |
| SEQ ID. NO: 3 | 5'TCCTTCC3' |
| SEQ ID. NO: 4 | 5'CGCCATCCT3' |
| SEQ ID. NO: 5 | 5'ATCCTTCCC3' |
| SEQ ID. NO: 6 | 5'GCGCCATCCTT3' |
| SEQ ID. NO: 7 | 5'GCCATCCTTCC3' |
| SEQ ID. NO: 8 | 5'GTGCGCCATCCTTCC3' |
| SEQ ID. NO: 9 | 5'TGCGCCATCCTTCCC3' |
| SEQ ID. NO: 10 | 5'TCGCCACTCGATCCTGCCCG3' |

Example 2

Incorporation of Oligonucleotides into Liposomes

Liposomal p-Ethoxy Oligonucleotides p-Ethoxy-oligonucleotides (also referred to as pE oligos) are dissolved in DMSO and the phospholipids (Avanti Polar Lipids, Alabaster, Ala.), for example the preferred neutral phospholipid dioleoylphosphatidylcholine (DOPC), is dissolved in tert-butanol. The lipid is then mixed with the antisense oligonucleotides. In the case of DOPC, the ratio of the lipid to the antisense oligos is 20:1. Tween 20 is added to the lipid:oligo mixture such that Tween 20 is 5% of the combined weight of the lipid and oligo. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used upto three months. When required the lyophilized liposomes are reconstituted in 0.9% saline. The average diameter of the particles obtained using Tween 20 for encapsulating the lipid with the oligo is 0.7-1.0 µm in diameter.

Example 3

Cell Line and Viability Assays

Cell Line

CJ cells, a human transformed follicular lymphoma cell line bearing the t(14;18) translocation which overexpresses Bcl-2 protein, were used. CJ cells were grown in RPMI 1640 media (GIBCO, Grand Island, N.Y.) supplemented with 10% heat-inactivated fetal bovine serum (FBS).

Delivery of Liposomal Antisense Oligonucleotides to Cells

Thirty thousand cells/well were seeded in a 96-well plate in 0.1 mL of the respective medium. Cells were incubated with liposomal antisense oligonucleotides at final concentration of 2 to 12 µmol/L at 37° C. in a 5% $CO_2$ incubator. Each experiment was done in triplicate and repeated at least 6-7 times.

Cell Viability Assay

The viability of the neoplastic cells was measured by the MTS dye (Promega, Wis.). After 5 days of incubation with liposomal antisense oligonucleotides, 100 µL of fresh medium and 20 µL of MTS dye were added to each well. After incubation for 3-4 hours at 37° C., the plates were read directly on a microplate reader (Molecular Devices, CA) at 490 nm. All experiments were analyzed by t-test in which the viabilities of the cells treated with the liposomal antisense oligonucleotides were compared with those of the untreated controls.

Western Blots for Bcl-2 and Bax Protein

Figure 2:
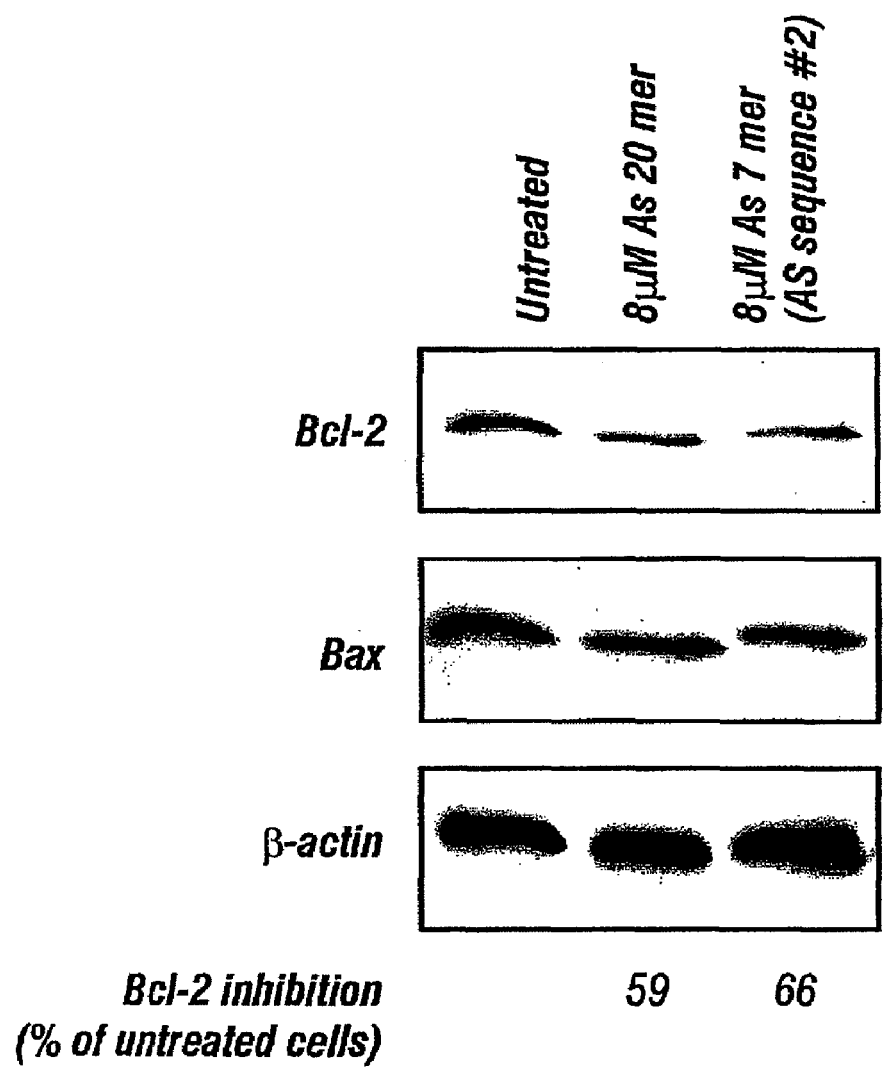
FIG. 2. Western Blot Analysis using Bcl-2 Antisense Oligonucleotides. β-actin and Bax are the Negative Controls.

One hundred thousand cells/well were seeded in a 6-well plate in 3 mL of the respective medium, treated with 8 µmol/L of the 20-mer and the 7-mers (i.e. SEQ ID Nos. 1 and 2) of the liposomal antisense oligonucleotides described in Table 3, and incubated at 37° C. for three days. Untreated cells were also maintained in culture. Samples were removed on day 3 after the addition of the liposomal antisense oligonucleotides and lysed in 100 µL of lysis buffer (1% Triton, 150 mmol/L NaCl and 25 mmol/L Tris pH 7.4) at 0° C. for 30 minutes. After centrifugation at 12,000×g for 10 minutes, the supernatants were recovered and normalized for total protein content. The lysates were mixed with sample buffer containing 1% of sodium dodecyl sulfate (SDS) and 1% B-mercaptoethanol and boiled for 5 minutes. SDS-PAGE was run on 12% polyacrylamide gels, electrophoretically transferred to nitrocellulose membranes and blocked in 5% non-fat dry milk. The membranes were incubated with the anti-human-Bcl-2 monoclonal antibody (Santa Cruz), or rabbit anti-human-Bax polyclonal antibody (Santa Cruz), with mouse anti-actin monoclonal antibody (Sigma). After washing and incubation with a peroxidase-labeled antirabbit or antimouse secondary antibody (Amersham), blots were developed by enhanced chemiluminescence system (Amersham). To estimate the inhibition of Bcl-2 protein and the ratio of Bcl-2/Bax proteins, bands were visualized by enhanced chemiluminescence and densitometric scans were performed on western blots on an AlphaImager 2000 densitometer. The AlphaImage application program was used to determine the ratio of Bcl-2:Actin and Bcl-2:Bax proteins. Results of the Western blot are shown in FIG. 2.

Effect of L-Bcl-2-Antisense Oligonucleotides ("L-Bcl-2") on Lymphoma Cell Growth Five days after the addition of 0-12 µmol/L of the L-Bcl-2 antisense oligonucleotides (of SEQ ID Nos. 1-10) to the cells, the viability of tumoral cells was assessed. Cell growth was inhibited in a concentration-dependent manner in CJ cells, which bear the t(14;18) translocation and expresses very high levels of Bcl-2. Sequence-dependent, size-dependent and dose-dependent decreases in cell viabilities were seen in three separate experiments (see data in Table 9).

TABLE 9

Effects of Various Liposomal Bcl-2 Antisense Sequences on the Viability of CJ Cells

| Antisense Sequence No. | Concentration of Liposomal Antisense Oligonucleotides (Percent Growth and Viability of CJ cells) | | |
|---|---|---|---|
|  | 2 µM | 6 µM | 10 µM |
| SEQ ID. NO: 1 Regular Bcl-2 AS (20-mer) | 75.2 | 35.4 | 0 |
| SEQ ID. NO: 10 Scrambled Bcl-2 (Control) (20-mer) | 121.0 | 80.5 | 85 |
| SEQ ID. NO: 2 (7-mer) | 104.1 | 78.6 | 57.4 |
| SEQ ID. NO: 3 (7-mer) | 62.1 | 6.0 | 0 |
| SEQ ID. NO: 4 (9-mer) | 87.6 | 77.3 | 49.5 |
| SEQ ID. NO: 5 (9-mer) | 96.2 | 66.3 | 37.6 |
| SEQ ID. NO: 6 (11-mer) | 77.4 | 39.8 | 8.9 |
| SEQ ID. NO: 7 (11-mer) | 63.7 | 62.3 | 66.9 |
| SEQ ID. NO: 8 (15-mer) | 64.5 | 54.2 | 20.0 |
| SEQ ID. NO: 9 (15-mer) | 76.2 | 53.0 | 35.3 |

The ability of the short oligonucleotides to influence cell-viability and growth inhibition were compared with respect to the oligonucleotide encoded by SEQ ID. NO: 1 which is a 20-mer bcl-2 antisense oligonucleotide. A scrambled bcl-2 sequence was used as a negative control.

L-bcl-2 Selectively Downregulates the Expression of Bcl-2 Protein and Cell Growth in a Dose-Dependent Manner The inhibition in cell growth was seen in the CJ follicular lymphoma cell line which bears the t(14;18) translocation. There was no non-specific toxicity in CJ cells exposed to the control oligonucleotide. The growth inhibitory effects could be observed starting at a concentration of 3 µmol/L of L-bcl-2, and the inhibitory effects were maximal at 3-8 µmol/L concentration depending on the sequence and length of the specific oligonucleotide (FIG. 1A-1H). Furthermore, both the short (7-mer) and the long (20-mer) Bcl-2 could inhibit the expression of Bcl-2 protein to a similar extent (59% vs 62%). The Bcl-2-protein inhibition is specific because Bcl-2 did not inhibit Bax and Actin expression. Thus, the inhibition of Bcl-2 protein leads to cell growth inhibition in cells that are dependent on the presence of Bcl-2 protein for maintaining viability.

Example 4

In Vivo Testing

In an initial round of in vivo trials, inventors will use a mice model of human cancer with the histologic features and metastatic potential resembling tumors seen in humans and treat these animals with lipid-associated poly- or oligonucleotide compositions to examine the suppression of tumor development.

These studies are based on the discovery that short bcl-2 antisense oligonucleotides associated with lipids inhibit the production of the Bcl-2 protein and the growth of t(14;18) translocation bearing cells as described above. The Examples above further show that these lipid formulations inhibit the growth of bcl-2-related cancer cells. The current example uses lipid-associated short oligonucleotide formulations, either alone or in combination with chemotherapeutic drugs, to provide a useful preventive and therapeutic regimen for patients with bcl-2-overexpressing cancers.

Mice of a suitable cancer model (see, e.g., McDonnell, 1993) will be treated with doses of the lipid-associated short oligonucleotide compositions or the lipid-associated specific oligonucleotides represented by the sequences in SEQ ID NO: 6, SEQ ID. NO: 7, SEQ ID. NO: 8 and SEQ ID. NO: 9 starting at 8-10 weeks of age or approximately 25 g in weight. The mice used may be transgenic mice bearing the t(14;18) translocation, or they may be nude or SCID mice that were implanted intraperitoneally with human follicular lymphoma cell lines. Several combinations and concentrations of these formulations will be tested. Three groups of mice will be used: untreated mice (i.e., mice injected with buffer only), mice injected with the liposomal short antisense oligos or the lipid-associated specific oligonucleotides represented by the sequences in SEQ ID NO: 6, SEQ ID. NO: 7, SEQ ID. NO: 8 and SEQ ID. NO: 9, and mice injected with liposomal control oligos. The animals will be injected intravenously with liposomal short oligos twice a week. The doses will range between 0-15 mg of liposomal short oligos per kg of mouse in weight. The treatments will be from 6 to 8 weeks.

The effect of the lipid-associated short oligonucleotide compositions or the lipid-associated specific oligonucleotides represented by the sequences in SEQ ID NO: 6, SEQ ID. NO: 7, SEQ ID. NO: 8 and SEQ ID. NO: 9 on the development of follicular lymphoma tumors will be compared with the control group by measuring tumor size, mouse survival, B cell hyperplasia, and Bcl-2 expression. It is predicted that, unlike the control groups of mice that will develop tumors, the testing group of mice will have decreased Bcl-2 expression, B cell hyperplasia, and tumor size, as well as prolonged survival. The group treated with liposomal control oligos should have no such effects.

Example 5

Clinical Trials

This example is concerned with the development of human treatment protocols using the lipid-associated short oligonucleotide compositions or the lipid-associated specific oligonucleotides represented by the sequences in SEQ ID NO: 6, SEQ ID. NO: 7, SEQ ID. NO: 8 and SEQ ID. NO: 9. These lipid formulations will be of use in the clinical treatment of various bcl-2-overexpressing cancers and diseases in which transformed or cancerous cells play a role. Such treatment will be particularly useful tools in anti-tumor therapy, for example, in treating patients with follicular lymphoma. This treatment will also be useful in treating other conditions that are mediated by bcl-2 over-expression and resistant to conventional regimens and treatments such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

The various elements of conducting a clinical trial, including patient treatment and monitoring, will be known to those of skill in the art in light of the present disclosure. The following information is being presented as a general guideline for use in establishing lipid-associated short oligonucleotide compositions alone or in combinations with other anti-cancer drugs in clinical trials.

Candidates for the phase 1 clinical trial will be patients on which all conventional therapies have failed. Liposomal Bcl-2 antisense short oligos and/or the lipid-associated specific oligonucleotides represented by the sequences in SEQ ID NO: 6, SEQ ID. NO: 7, SEQ ID. NO: 8 and SEQ ID. NO: 9 will be administered to them intravenously on a tentative weekly basis. To monitor disease course and evaluate the anti-tumor responses, it is contemplated that the patients should be examined for appropriate tumor markers every month. To assess the effectiveness of the drug, the following parameters will be monitored: tumor size and bone marrow infiltration of the cancer cells. Tests that will be used to monitor the progress of the patients and the effectiveness of the treatments include: physical exam, X-ray, blood work and other clinical laboratory methodologies. In addition, peripheral blood and bone marrow samples will be drawn to assess the modification of the target protein expression. The doses given in the phase 1 study will be escalated as is done in standard phase 1 clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

Example 6

Human Treatment and Clinical Protocols

This example describes a protocol to facilitate the treatment of bcl-2-mediated diseases using lipid-associated short oligonucleotide compositions and/or the lipid-associated specific oligonucleotides represented by the sequences in SEQ ID NO: 6, SEQ ID. NO: 7, SEQ ID. NO: 8 and SEQ ID. NO: 9 alone or in combination with other anti-cancer drugs.

Typically, patients that are candidates for treatment are those with follicular lymphoma although patients with hematologic malignancies, both leukemias and lymphomas; solid tumors like those associated with breast, prostate and colon cancer; and immune disorders may also be treated with the methods of this invention. The typical course of treatment will vary depending upon the individual patient and disease being treated in ways known to those of skill in the art. For example, a patient with follicular lymphoma might be treated in eight week cycles, although longer duration may be used if no adverse effects are observed with the patient, and shorter terms of treatment may result if the patient does not tolerate the treatment as hoped. Each cycle will consist of between 20 and 35 individual doses spaced equally, although this too may be varied depending on the clinical situation.

A patient presenting a bcl-2-mediated condition, like follicular lymphoma, may be treated using the following protocol. Patients may, but need not, have received previous chemo-, radio- or gene therapeutic treatments. Optimally the patient will exhibit adequate bone marrow function (defined as peripheral absolute granulocyte count of >2,000/mm$^3$ and platelet count of 100,000/mm$^3$, adequate liver function (bilirubin 1.5 mg/dl) and adequate renal function (creatinine 1.5 mg/dl).

The over-expression of bcl-2 is typically monitored before, during, and after the therapy. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The lipid-associated short oligo-nucleotide compositions and/or the lipid-associated specific oligonucleotides represented by the sequences in SEQ ID NO: 6, SEQ ID. NO: 7, SEQ ID. NO: 8 and SEQ ID. NO: 9 may be delivered to the patient before, after or concurrently with the other anti-cancer agents.

A typical treatment course may comprise about six doses delivered over a 7 to 21 day period. Upon election by the clinician the regimen may be continued with six doses every three weeks or on a less frequent (monthly, bimonthly, quarterly etc.) basis. Of course, these are only exemplary times for treatment, and the skilled practitioner will readily recognize that many other time-courses are possible.

To kill bcl-2-overexpressing cancer cells using the methods and compositions described in the present invention one will generally contact a target cell with the lipid-associated formulations described previously. These compositions will be provided in an amount effective to kill or inhibit the proliferation of the cell.

Regional delivery of the lipid-associated formulations will be an efficient method for delivering a therapeutically effective dose to counteract the clinical disease. Alternatively systemic delivery may be appropriate. The therapeutic composition of the present invention may be administered to the patient directly at the site of the tumor. This is in essence a topical treatment of the surface of the cancer. The volume of the composition should usually be sufficient to ensure that the entire surface of the tumor is contacted by the lipid-associated short oligonucleotide composition and/or the lipid-associated specific oligonucleotides represented by the sequences in SEQ ID NO: 6, SEQ ID. NO: 7, SEQ ID. NO: 8 and SEQ ID. NO: 9.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

Of course, the above-described treatment regimes may be altered in accordance with the knowledge gained from clinical trials such as those described in Example 5. Those of skill in the art will be able to take the information disclosed in this specification and optimize treatment regimes based on the clinical trials described in the specification.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aisenberg, "Coherent view of non-Hodgkin's lymphoma," *J. Clin. Oncol.,* 13:2656, 1995.

Akhtar et al., "Interactions of antisense DNA oligonucleotide analogs with phospholipids membranes (liposomes)," *Nucleic Acids Res.,* 19:5551, 1991.

Baichwal and Sugden, "Vectors for gene transfer derived from animal DNA viruses: Transient and stable expression of transferred genes," In: Kucherlapati R, (ed.) Gene transfer. New York: Plenum Press, pp. 117-148, 1986.

Bakhshi et al., "Cloning the chromosomal breakpoint of t(14;18) human lymphomas: clustering around JH on chromosome 14 and near a transcriptional unit on 18," *Cell,* 41:899, 1985.

Bangham et al., J. Mol. Biol., 13:238, 1965. Benvenisty and Neshif, "Direction introduction of genes into rats and expression of the genes," *Proc. Nat'l Acad. Sci. USA,* 83:9551, 1986.

Boise et al., "BCL-X, a BCL-2-related gene that functions as a dominant regulator of apoptotic cell death," *Cell,* 74:597, 1993.

Campos et al., "Effects of BCL-2 Antisense Oligodeoxynucleotides on In Vitro Proliferation and Survival of Normal Marrow Progenitors and Leukemic Cells," *Blood,* 84:595, 1994.

Chang et al., "Foreign gene delivery and expression in hepatocytes using a hepatitis B virus vector," *Hepatology,* 14:134A, 1991.

Chen and Okayama, "High-efficiency transfection of mammalian cells by plasmid DNA," *Mol. Cell Biol.,* 7:2745-2752, 1987.

Chittenden et al., "Induction of apoptosis by the Bcl-2 homologue Bak," *Nature,* 374:733, 1995.

Coffin, "Retroviridae and their replication," In: *Virology,* Fields et al. (eds.), New York: Raven Press, pp. 1437-1500, 1990.

Cotter et al., "Antisense oligonucleotides suppress B-cell lymphoma growth in a SCID-hu mouse model," *Oncogene,* 9:3049, 1994.

Coupar et al., "A general method for the construction of recombinant vaccinia virus expressing multiple foreign genes," *Gene,* 68:1-10, 1988.

Deamer and Uster, "Liposome Preparation: Methods and Mechanisms," *LIPOSOMES,* M. Ostro ed. (1983).

Dubensky et al., "Direct transfection of viral and plasmid DNA into the liver or spleen of mice," *Proc, Nat'l Acad. Sci. USA,* 81:7529-7533, 1984.

Fecheimer et al., "Transfection of mammalian cells with plasmid DNA by scrape loading and sonication loading," *Proc. Nat'l Acad. Sci. USA,* 76:3348-52, 1979.

Fraley et al., "Entrapment of a bacterial plasmid in phospholipid vesicles: Potential for gene transfer," *Proc. Nat'l Acad. Sci. USA,* 76:3348-3352, 1979.

Friedman et al., "CCAAT/enhancer-binding protein activates the promoter of the serum albumin gene in cultured hepatoma cells," *Genes Devel.* 3:1314, 1989.

Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87-104, 1991.

Gopal, "Gene transfer method for transient gene expression, stable transfection, and cotransfection of suspension cell cultures," *Mol. Cell Biol.*, 5:1188-1190, 1985.

Graham and van der Eb, "A new technique for the assay of infectivity of human adenovirus DNA", *Virology*, 52:456-467, 1973.

Graham et al., "Characteristics of a human cell line transformed by DNA from human adenovirus type 5 DNA", *J. Gen. Virol.*, 36:59-72, 1977.

Graninger et al., "Expression of bcl-2 and bcl-2-Ig fusion transcripts in normal and neoplastic cells," *J. Clin. Invest.*, 80:1512, 1987.

Gregoriadis, DRUG CARRIERS IN BIOLOGY AND MEDICINE, G. Gregoriadis (ed.), 1979.

Grunhaus & Horwitz, "Adenovirus as cloning vector," *Seminar in Virology*, 3:237-252, 1992.

Harland and Weintraub, "Translation of mammalian mRNA injected into Xenopus oocytes is specifically inhibited by antisense RNA," *J. Cell Biol.*, 101:1094-1099, 1985.

Hermonat and Muzycska, "Use of adenoassociated virus as a mammalian DNA cloning vector: Transduction of neomycin resistance into mammalian tissue culture cells," *Proc. Nat'l Acad. Sci. USA*, 81:6466-6470, 1984.

Hockenbery et al., 'Bcl-2 is an inner mitochondrial membrane protein that blocks programmed cell death," *Nature*, 348:334, 1990.

Horwich et al., "Synthesis of hepadenovirus particles that contain replication-defective duck hepatitis B virus genomes in cultured HuH7 cells," *J. Virol.* 64:642-650, 1990.

Johnson et al., "Patterns of survival in patients with recurrent follicular lymphoma: A 20-year study from a single center," *J. Clin. Oncol.*, 13:140, 1995.

Kaneda et al., "Increased expression of DNA cointroduced with nuclear protein in adult rat liver," *Science*, 243:375-378, 1989.

Kato et al., "Expression of hepatitis B virus surface antigen in adult rat liver," *J. Biol. Chem.*, 266:3361-3364, 1991.

Kiefer et al., "Modulation of apoptosis by the widely distributed Bcl-2 homologue Bak," *Nature*, 374: 736, 1995.

Kitada et al., "Investigations of antisense oligonucleotides targeted against bcl-2 RNAs," *Antisense Res. Dev.*, 3:157, 1993.

Klein et al., "High-velocity microprojectiles for delivering nucleic acids into living cells," *Nature*, 327:70-73, 1987.

Kozopas et. al "MCL-1, a gene expressed in programmed myeloid cell differentiation, has sequence similarity to BCL-2," *Proc. Nat'l Acad. Sci. USA*, 90:3516, 1993.

Lin et al., "Characterization of A 1, a novel hemopoietic-specific early-response gene with sequence similarity to BCL-2," *J. Immunol.*, 151:1979, 1993.

Mann et al., "Construction of a retrovirus packaging mutant and its uses to produce helper-free defective retrovirus," *Cell*, 33:153-159, 1983.

McDonnell, "The bcl-2-Immunoglobulin Transgenic Mouse: A Model of the t(14;18) Translocation in Human Follicular Lymphoma," *Transgene*, 1:47, 1993.

McDonnell and Korsmeyer, "Progression from lymphoid hyperplasia to high-grade malignant lymphoma in mice transgenic for the t(14;18)," *Nature*, 349:254, 1991.

McDonnell et al., "Bcl-2-immunoglobulin transgenic mice demonstrate extended B cell survival and follicular lymphoproliferation," *Cell*, 57:79, 1989.

Neilan et al., "An African Swine fever virus with similarity to the protooncogene BCL-2 and the Epstein-Barr virus gene BHRF1," *J. Virol.*, 67:4391, 1993.

Nicolas and Rubenstein, "Retroviral vectors," In: *Vectors: A survey of molecular cloning vectors and their uses*, Rodriguez and Denhardt, (eds.), Stoneham: Butterworth, pp. 494-513, 1988.

Nicolau et al., "Liposomes as carriers for in vivo gene transfer and expression," *Methods Enzymol.*, 149:157-176, 1987.

Nicolau and Sene, "Liposome-mediated DNA transfer in eukaryotic cells," *Biochem. Biophys. Acta*, 721:185-190, 1982.

Nuñez et al., "Deregulated BCL-2 gene expression selectively prolongs survival of growth factors-deprived hemopoietic cell lines," *J. Immunol.*, 144:3602, 1990.

Oltvai et al., "Bcl-2 heterodimerizes in vivo with a conserved homolog, bax, that accelerates programmed cell death," *Cell*, 74:609, 1993.

Paskind et al., "Dependence of moloney murine leukemia virus production on cell growth," *Virology*, 67:242-248, 1975.

Pearson et al., "Identification of an Epstein-Barr virus early gene encoding a second component of the restricted early antigen complex," *Virology*, 160:151, 1987.

Potter et al., "Enhancer-dependent expression of human k immunoglobulin genes introduced into mouse pre-B lymphocytes by electroporation," *Proc. Nat'l Acad. Sci. USA*, 81:7161-7165, 1984.

Reed, "Bcl-2: prevention of apoptosis as a mechanism of drug resistance," *Hematol. Oncol. Clin. North Am.*, 9:451, 1995.

Reed et al., "Antisense-mediated inhibition of bcl-2 protooncogene expression and leukemic cell growth and survival: comparisons of phosphodiester and phosphorothioate oligodeoxynucleotides," Cancer Research, 50: 6565, 1990a.

Reed et al., "Bcl-2-mediated tumorigenicity in a human T-lymphoid cell line: synergy with c-myc and inhibition by Bcl-2 antisense," *Proc. Nat'l Acad. Sci. USA*, 87:3660, 1990b.

Ridgeway, "Mammalian expression vectors," In: Rodriguez R L, Denhardt D T, (ed.)

Vectors: A survey of molecular cloning vectors and their uses. Stoneham: Butterworth, pp. 467-492, 1988.

Rippe et al., "DNA-mediated gene transfer into adult rat hepatocytes in primary culture," *Mol. Cell Biol.*, 10:689-695, 1990.

Sato et al., "Investigations of bcl-2 protein family interactions using yeast two-hybrid system," *Proc. Nat'l Acad. Sci. USA*, 91:9238, 1994.

Stratford-Perricaudet and Perricaudet, "Gene transfer into animals: the promise of adenovirus," pp. 51-61, In: *Human Gene Transfer*, Eds, O. Cohen-Haguenauer and M. Boiron Editions John Libbey Exrotext, France, 1991.

Szoka and Papahadjopoulos, *Proc. Nat'l Acad. Sci. U.S.A.* 75:4194-98 (1978).

Tari et al., "Liposomal delivery of methylphosphonate antisense oligodeoxynucleotides in chronic myelogenous leukemia," *Blood*, 84:601, 1994.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149-188, 1986.

Tsujimoto et al., "Characterization of the protein product of bcl-2, the gene involved in human follicular lymphoma," *Oncogene*, 2:3, 1987.

Tsujimoto and Croce, "Analysis of the Structure, Transcripts, and Protein Products of bcl-2, the gene involved in Human Follicular," *Proc. Natl. Acad. Sci. USA,* 83:5214, 1986.

Tsujimoto et al., "The t(14;18) chromosome translocation involved in B-cell neoplasms result from mistakes in VDJ joining," *Science,* 229:1390, 1985.

Tur-Kaspa et al., "Use of electroporation to introduce biologically active foreign genes into primary rat hepatocytes," *Mol. Cell Biol.,* 6:716-718, 1986.

U.S. Pat. No. 5,734,033, Reed et al., 1998a.

U.S. Pat. No. 5,831,066, Reed 1998b.

U.S. Pat. No. 5,837,838 Reed et al., 1998c.

Wagner et al., *Science,* 260:1510-1513, 1993.

Wong et al., "Appearance of β-lactamase activity in animal cells upon liposome mediated gene transfer," *Gene,* 10:87-94, 1980.

Wu and Wu, "Evidence for targeted gene delivery to HepG2 hepatoma cells in vitro," *Biochemistry,* 27:887-892, 1988.

Wu and Wu, "Receptor-mediated in vitro gene transfections by a soluble DNA carrier system," *J. Biol. Chem.,* 262: 4429-4432, 1987.

Yang et al., "Bad, a heterodimeric partner for Bcl-$X_L$ and Bcl-2, displaces Bax and promotes cell death," *Cell,* 80:285, 1995.

Yang et al., "In vitro and in vitro gene transfer to mammalian somatic cells by particle bombardment," *Proc. Nat'l Acad. Sci. USA,* 87:9568-9572, 1990.

Yin et al., "BH1 and BH2 domains of Bcl-2 are required for inhibition of apoptosis and heterodimerization with Bax," *Nature,* 369: 321, 1994.

Zelenin et al., "High-velocity mechanical DNA transfer of the chloramphenicol acetyltransferase gene into rodent liver, kidney and mammary gland cells in organ explants and in vivo," *FEBS Lett.,* 280:94-96, 1991.

---

What is claimed is:

1. A method of inhibiting a Bcl-2-associated tumor comprising:
   a) obtaining a composition comprising an antisense oligonucleotide that is complementary to a Bcl-2 oligonucleotide wherein the antisense oligonucleotide comprises the sequence 5'CGCCATCCT3' (SEQ ID NO:4) or the sequence 5'ATCCTTCCC3' (SEQ ID NO:5), combined with a substantially uncharged lipid component and a pharmaceutically acceptable carrier, wherein the lipid component comprises a neutral lipid, or a mixture of lipids, to provide the substantially uncharged lipid component; and
   c) administering said composition to a cancer cell, wherein said cancer cell is in a human and wherein said mixture is delivered to said human in an amount of from about 5 to about 30 mg oligonucleotide per m$^2$.

2. The method of claim 1, wherein said composition mixture is administered three times per week for eight weeks.

3. The method of claim 1, wherein said lipid component comprises a neutral lipid.

4. The method of claim 1, wherein the antisense oligonucleotide includes a region complementary to a region of the translation initiation site of Bcl-2 mRNA.

5. The method of claim 3, wherein the neutral lipid comprises a phosphatidylcholine, a phosphatidylglycerol, or a phosphatidylethanolamine.

6. The method of claim 5, wherein the phosphatidylcholine comprises dioleoylphosphatidylcholine.

7. The method of claim 3, wherein the lipid component comprises a mixture of lipids to provide a substantially uncharged lipid mixture.

8. The method of claim 7, wherein the lipid mixture comprises negatively and positively charged lipids.

9. The method of claim 1, wherein the antisense oligonucleotide is a phosphodiester oligonucleotide.

10. The method of claim 1, wherein the antisense oligonucleotide is a nuclease-resistant oligonucleotide.

11. The method of claim 10, wherein said nuclease-resistant oligonucleotide is a p-ethoxy oligonucleotide.

12. The method of claim 10, wherein said nuclease-resistant oligonucleotide is a phosphorothioate oligonucleotide.

13. The method of claim 1, wherein the antisense oligonucleotide comprises the sequence 5'CGCCATCCT3' (SEQ ID NO:4).

14. The method of claim 1, wherein the antisense oligonucleotide comprises the sequence 5'ATCCTTCCC3' (SEQ ID NO:5).

15. The method of claim 1, wherein said cancer cell is a follicular lymphoma cell, a breast cancer cell, a prostate cancer cell, liver cancer cell, a pancreatic cancer cell, a lung cancer cell, a brain cancer cell, an ovarian cancer cell, a testicular cancer cell, a skin cancer cell, a leukemia cell, a head and neck cancer cell, an esophageal cancer cell, a stomach cancer cell, a kidney cancer cell, a colon cancer cell or a rectal cancer cell.

16. The method of claim 1, wherein the lipid component comprises liposomes that encapsulate the antisense oligonucleotide.

17. The method of claim 1, wherein said composition is delivered to said human in a volume of 0.50-10.0 ml per dose.

* * * * *

UNITED STATES PATENT AND TRADEMARK OFFICE
CERTIFICATE OF CORRECTION

PATENT NO. : 7,704,962 B1 Page 1 of 1
APPLICATION NO. : 09/506979
DATED : April 27, 2010
INVENTOR(S) : Ana M. Tari et al.

It is certified that error appears in the above-identified patent and that said Letters Patent is hereby corrected as shown below:

In claim 2, column 45, lines 30-31, delete "mixture".

Signed and Sealed this

Thirteenth Day of July, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
cagcgtgcgc catccttccc                                                  20

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2 gccatcc                                                                 7

<210> SEQ ID NO 3
<211> LENGTH: 7
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3 tccttcc                                                                 7

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4 cgccatcct                                                               9
```

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5 atccttccc                                                               9

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcgccatcct t                                                           11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gccatccttc c                                                           11

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gtgcgccatc cttcc                                                       15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tgcgccatcc ttccc                                                       15

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
tcgccactcg atcctgcccg                                                  20

```
<210> SEQ ID NO 11
<211> LENGTH: 5087
<212> TYPE: DNA
<213> ORGANISM: Artificial Sequence
<220> FEATURE:
<221> NAME/KEY: CDS
<222> LOCATION: (1459)..(2175)
<220> FEATURE:
<223> OTHER INFORMATION: Description of Artificial Sequence: Synthetic
      Primer

<400> SEQUENCE: 11
gcgcccgccc ctccgcgccg cctgcccgcc cgcccgccgc gctccgccc gccgctctcc      60 gtggccccgc cgcgctgccg ccgccgccgc tgccagcgaa ggtgccgggg ctccgggccc     120
tccctgccgg cggccgtcag cgctcggagc gaactgcgcg acgggaggtc cgggaggcga     180
ccgtagtcgc gccgccgcgc aggaccagga ggaggagaaa gggtgcgcag cccggaggcg     240
gggtgcgccg gtgggtgca gcggaagagg gggtccaggg gggagaactt cgtagcagtc      300 atcctttta ggaaaagagg gaaaaaataa aaccctcccc caccacctcc ttctccccac      360
ccctcgccgc accacacaca gcgcgggctt ctagcgctcg gcaccggcgg gccaggcgcg     420
tcctgccttc atttatccag cagcttttcg gaaaatgcat ttgctgttcg gagtttaatc     480
agaagacgat tcctgcctcc gtccccggct ccttcatcgt cccatctccc ctgtctctct     540
cctggggagg cgtgaagcgg tcccgtggat agagattcat gcctgtgtcc gcgcgtgtgt     600
gcgcgcgtat aaattgccga gaaggggaaa acatcacagg acttctgcga ataccggact     660
gaaaattgta attcatctgc cgccgccgct gccaaaaaaa aactcgagct cttgagatct     720
ccggttggga ttcctgcgga ttgacatttc tgtgaagcag aagtctggga atcgatctgg     780
aaatcctcct aatttttact ccctctcccc ccgactcctg attcattggg aagtttcaaa     840
tcagctataa ctggagagtg ctgaagattg atgggatcgt tgccttatgc atttgttttg     900
gttttacaaa aaggaaactt gacagaggat catgctgtac ttaaaaaata caagtaagtc     960
tcgcacagga aattggttta atgtaacttt caatggaaac ctttgagatt ttttacttaa    1020
agtgcattcg agtaaattta atttccaggc agcttaatac attgttttta gccgtgttac    1080
ttgtagtgtg tatgccctgc tttcactcag tgtgtacagg gaaacgcacc tgatttttta    1140
cttattagtt tgttttttct ttaacctttc agcatcacag aggaagtaga ctgatattaa    1200
caatacttac taataataac gtgcctcatg aaataaagat ccgaaaggaa ttggaataaa    1260
aatttcctgc gtctcatgcc aagagggaaa caccagaatc aagtgttccg cgtgattgaa    1320
gacaccccct cgtccaagaa tgcaaagcac atccaataaa atagctggat tataactcct    1380
cttctttctc tgggggccgt ggggtgggag ctggggcgag aggtgccgtt ggccccgtt    1440 gcttttcctc tgggaagg atg gcg cac gct ggg aga acg ggg tac gac aac     1491
                    Met Ala His Ala Gly Arg Thr Gly Tyr Asp Asn
                     1               5                  10 cgg gag ata gtg atg aag tac atc cat tat aag ctg tcg cag agg ggc    1539
Arg Glu Ile Val Met Lys Tyr Ile His Tyr Lys Leu Ser Gln Arg Gly
             15                  20                  25 tac gag tgg gat gcg gga gat gtg ggc gcc gcg ccc ccg ggg gcc gcc    1587
Tyr Glu Trp Asp Ala Gly Asp Val Gly Ala Ala Pro Pro Gly Ala Ala
         30                  35                  40 ccc gca ccg ggc atc ttc tcc tcc cag ccc ggg cac acg ccc cat cca    1635
Pro Ala Pro Gly Ile Phe Ser Ser Gln Pro Gly His Thr Pro His Pro
     45                  50                  55 gcc gca tcc cgc gac ccg gtc gcc agg acc tcg ccg ctg cag acc ccg    1683
```

-continued

| | | | | | | | | | | | | | | | |
|---|---|---|---|---|---|---|---|---|---|---|---|---|---|---|---|
| Ala | Ala | Ser | Arg | Asp | Pro | Val | Ala | Arg | Thr | Ser | Pro | Leu | Gln | Thr | Pro |
| 60 | | | | | 65 | | | | 70 | | | | | 75 | |

```
gct gcc ccc ggc gcc gcc gcg ggg cct gcg ctc agc ccg gtg cca cct    1731
Ala Ala Pro Gly Ala Ala Ala Gly Pro Ala Leu Ser Pro Val Pro Pro
            80                  85                  90 gtg gtc cac ctg gcc ctc cgc caa gcc ggc gac gac ttc tcc cgc cgc    1779
Val Val His Leu Ala Leu Arg Gln Ala Gly Asp Asp Phe Ser Arg Arg
            95                 100                 105 tac cgc ggc gac ttc gcc gag atg tcc agc cag ctg cac ctg acg ccc    1827
Tyr Arg Gly Asp Phe Ala Glu Met Ser Ser Gln Leu His Leu Thr Pro
        110                 115                 120 ttc acc gcg cgg gga cgc ttt gcc acg gtg gtg gag gag ctc ttc agg    1875
Phe Thr Ala Arg Gly Arg Phe Ala Thr Val Val Glu Glu Leu Phe Arg
    125                 130                 135 gac ggg gtg aac tgg ggg agg att gtg gcc ttc ttt gag ttc ggt ggg    1923
Asp Gly Val Asn Trp Gly Arg Ile Val Ala Phe Phe Glu Phe Gly Gly
140                 145                 150                 155 gtc atg tgt gtg gag agc gtc aac cgg gag atg tcg ccc ctg gtg gac    1971
Val Met Cys Val Glu Ser Val Asn Arg Glu Met Ser Pro Leu Val Asp
                160                 165                 170 aac atc gcc ctg tgg atg act gag tac ctg aac cgg cac ctg cac acc    2019
Asn Ile Ala Leu Trp Met Thr Glu Tyr Leu Asn Arg His Leu His Thr
            175                 180                 185 tgg atc cag gat aac gga ggc tgg gat gcc ttt gtg gaa ctg tac ggc    2067
Trp Ile Gln Asp Asn Gly Gly Trp Asp Ala Phe Val Glu Leu Tyr Gly
        190                 195                 200 ccc agc atg cgg cct ctg ttt gat ttc tcc tgg ctg tct ctg aag act    2115
Pro Ser Met Arg Pro Leu Phe Asp Phe Ser Trp Leu Ser Leu Lys Thr
    205                 210                 215 ctg ctc agt ttg gcc ctg gtg gga gct tgc atc acc ctg ggt gcc tat    2163
Leu Leu Ser Leu Ala Leu Val Gly Ala Cys Ile Thr Leu Gly Ala Tyr
220                 225                 230                 235 ctg agc cac aag tgaagtcaac atgcctgccc caaacaaata tgcaaaggt         2215
Leu Ser His Lys tcactaaagc agtagaaata atatgcattg tcagtgatgt accatgaaac aaagctgcag  2275
gctgtttaag aaaaaataac acacatataa acatcacaca cacagacaga cacacacaca  2335
cacaacaatt aacagtcttc aggcaaaacg tcgaatcagc tatttactgc caaagggaaa  2395
tatcatttat ttttacatt attaagaaaa aagatttatt tatttaagac agtcccatca   2455
aaactccgtc tttggaaatc cgaccactaa ttgccaaaca ccgcttcgtg tggctccacc  2515
tggatgttct gtgcctgtaa acatagattc gctttccatg ttgttggccg atcaccatc   2575 tgaagagcag acggatggaa aaaggacctg atcattgggg aagctggctt tctggctgct  2635
ggaggctggg gagaaggtgt tcattcactt gcatttcttt gccctggggg cgtgatatta  2695
acagagggag ggttcccgtg gggggaagtc catgcctccc tggcctgaag aagagactct  2755
ttgcatatga ctcacatgat gcatacctgg tgggaggaaa agagttggga acttcagatg  2815
gacctagtac ccactgagat tccacgccg aaggacagcg atgggaaaaa tgcccttaaa   2875
tcataggaaa gtattttttt aagctaccaa ttgtgccgag aaaagcattt tagcaattta  2935
tacaatatca tccagtacct taaaccctga ttgtgtatat tcatatattt tggatacgca  2995
ccccccaact cccaatactg gctctgtctg agtaagaaac agaatcctct ggaacttgag  3055
gaagtgaaca tttcggtgac ttccgatcag gaaggctaga gttacccaga gcatcaggcc  3115
gccacaagtg cctgctttta ggagaccgaa gtccgcagaa cctacctgtg tcccagcttg  3175
gaggcctggt cctggaactg agccgggccc tcactggcct cctccaggga tgatcaacag  3235
```

-continued

```
ggtagtgtgg tctccgaatg tctggaagct gatggatgga gctcagaatt ccactgtcaa    3295
gaaagagcag tagaggggtg tggctgggcc tgtcaccctg ggccctcca ggtaggcccg     3355 ttttcacgtg gagcatagga gccacgaccc ttcttaagac atgtatcact gtagagggaa    3415
ggaacagagg ccctgggcct tcctatcaga aggacatggt gaaggctggg aacgtgagga    3475
gaggcaatgg ccacggccca ttttggctgt agcacatggc acgttggctg tgtggccttg    3535
gccacctgtg agtttaaagc aaggctttaa atgactttgg agagggtcac aaatcctaaa    3595
agaagcattg aagtgaggtg tcatggatta attgacccct gtctatggaa ttacatgtaa    3655
aacattatct tgtcactgta gtttggtttt atttgaaaac ctgacaaaaa aaagttcca    3715 ggtgtggaat atgggggtta tctgtacatc ctggggcatt aaaaaaaat caatggtggg    3775 gaactataaa gaagtaacaa agaagtgac atcttcagca aataaactag gaaatttttt    3835
tttcttccag tttagaatca gccttgaaac attgatggaa taactctgtg cattattgc    3895 attatatacc atttatctgt attaactttg gaatgtactc tgttcaatgt taatgctgt    3955 ggttgatatt tcgaaagctg ctttaaaaaa atacatgcat ctcagcgttt ttttgttttt    4015
aattgtattt agttatggcc tatacactat ttgtgagcaa aggtgatcgt tttctgtttg    4075
agatttttat ctcttgattc ttcaaaagca ttctgagaag gtgagataag ccctgagtct    4135
cagctaccta agaaaaacct ggatgtcact ggccactgag gagctttgtt tcaaccaagt    4195
catgtgcatt tccacgtcaa cagaattgtt tattgtgaca gttatatctg ttgtcccttt    4255
gaccttgttt cttgaaggtt tcctcgtccc tgggcaattc cgcatttaat tcatggtatt    4315
caggattaca tgcatgtttg gttaaaccca tgagattcat tcagttaaaa atccagatgg    4375
cgaatgacca gcagattcaa atctatggtg gtttgacctt tagagagttg ctttacgtgg    4435
cctgtttcaa cacagaccca cccagagccc tcctgccctc cttccgcggg ggctttctca    4495
tggctgtcct tcagggtctt cctgaaatgc agtggtcgtt acgctccacc aagaaagcag    4555
gaaacctgtg gtatgaagcc agacctcccc ggcgggcctc agggaacaga atgatcagac    4615 cttgaatga ttctaatttt taagcaaaat attattttat gaaaggttta cattgtcaaa    4675
gtgatgaata tggaatatcc aatcctgtgc tgctatcctg ccaaaatcat tttaatggag    4735
tcagtttgca gtatgctcca cgtggtaaga tcctccaagc tgctttagaa gtaacaatga    4795
agaacgtgga cgtttttaat ataaagcctg ttttgtcttt tgttgttgtt caaacgggat    4855
tcacagagta tttgaaaaat gtatatatat taagaggtca cggggggctaa ttgctagctg    4915 gctgccttt gctgtggggt tttgttacct ggttttaata acagtaaatg tgcccagcct    4975
cttggcccca gaactgtaca gtattgtggc tgcacttgct ctaagagtag ttgatgttgc    5035
attttcctta ttgttaaaaa catgttagaa gcaatgaatg tatataaaag cd              5087
```

<210> SEQ ID NO 12
<211> LENGTH: 239
<212> TYPE: PRT
<213> ORGANISM: Artificial Sequence
<220> FEATURE:
<223> OTHER INFORMATION: Description of Artificial Sequence: Synthetic Primer

<400> SEQUENCE: 12

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30
```

-continued

```
Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Val Val His Leu Ala
                 85                  90                  95

Leu Arg Gln Ala Gly Asp Asp Phe Ser Arg Arg Tyr Arg Gly Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235

<210> SEQ ID NO 13
<211> LENGTH: 911
<212> TYPE: DNA
<213> ORGANISM: Artificial Sequence
<220> FEATURE:
<221> NAME/KEY: CDS
<222> LOCATION: (147)..(761)
<220> FEATURE:
<223> OTHER INFORMATION: Description of Artificial Sequence:  Synthetic
      Primer

<400> SEQUENCE: 13
tgattgaaga cacccctcg tccaagaatg caaagcacat ccaataaaat agctggatta      60
taactcctct tctttctctg ggggccgtgg ggtgggagct ggggcgagag gtgccgttgg    120
cccccgttgc ttttcctctg ggaagg atg gcg cac gct ggg aga acg ggg tac    173
                             Met Ala His Ala Gly Arg Thr Gly Tyr
                               1               5 gac aac cgg gag ata gtg atg aag tac atc cat tat aag ctg tcg cag    221
Asp Asn Arg Glu Ile Val Met Lys Tyr Ile His Tyr Lys Leu Ser Gln
 10              15                  20                  25 agg ggc tac gag tgg gat gcg gga gat gtg ggc gcc gcg ccc ccg ggg    269
Arg Gly Tyr Glu Trp Asp Ala Gly Asp Val Gly Ala Ala Pro Pro Gly
             30                  35                  40 gcc gcc ccc gca ccg ggc atc ttc tcc tcc cag ccc ggg cac acg ccc    317
Ala Ala Pro Ala Pro Gly Ile Phe Ser Ser Gln Pro Gly His Thr Pro
         45                  50                  55 cat cca gcc gca tcc cgc gac ccg gtc gcc agg acc tcg ccg ctg cag    365
His Pro Ala Ala Ser Arg Asp Pro Val Ala Arg Thr Ser Pro Leu Gln
     60                  65                  70 acc ccg gct gcc ccc ggc gcc gcc gcg ggg cct gcg ctc agc ccg gtg    413
```

```
                                                                           -continued Thr Pro Ala Ala Pro Gly Ala Ala Ala Gly Pro Ala Leu Ser Pro Val
        75                  80                  85 cca cct gtg gtc cac ctg gcc ctc cgc caa gcc ggc gac gac ttc tcc          461
Pro Pro Val Val His Leu Ala Leu Arg Gln Ala Gly Asp Asp Phe Ser
 90              95                 100                 105 cgc cgc tac cgc ggc gac ttc gcc gag atg tcc agc cag ctg cac ctg          509
Arg Arg Tyr Arg Gly Asp Phe Ala Glu Met Ser Ser Gln Leu His Leu
                    110                 115                 120 acg ccc ttc acc gcg cgg gga cgc ttt gcc acg gtg gtg gag gag ctc          557
Thr Pro Phe Thr Ala Arg Gly Arg Phe Ala Thr Val Val Glu Glu Leu
                125                 130                 135 ttc agg gac ggg gtg aac tgg ggg agg att gtg gcc ttc ttt gag ttc          605
Phe Arg Asp Gly Val Asn Trp Gly Arg Ile Val Ala Phe Phe Glu Phe
            140                 145                 150 ggt ggg gtc atg tgt gtg gag agc gtc aac cgg gag atg tcg ccc ctg          653
Gly Gly Val Met Cys Val Glu Ser Val Asn Arg Glu Met Ser Pro Leu
        155                 160                 165 gtg gac aac atc gcc ctg tgg atg act gag tac ctg aac cgg cac ctg          701
Val Asp Asn Ile Ala Leu Trp Met Thr Glu Tyr Leu Asn Arg His Leu
170                 175                 180                 185 cac acc tgg atc cag gat aac gga ggc tgg gta ggt gca tct ggt gat          749
His Thr Trp Ile Gln Asp Asn Gly Gly Trp Val Gly Ala Ser Gly Asp
                    190                 195                 200 gtg agt ctg ggc tgaggccaca ggtccgagat cggggggttgg agtgcgggtg             801
Val Ser Leu Gly
            205 ggctcctggg caatgggagg ctgtggagcc ggcgaaataa aatcagagtt gttgcttccc        861 ggcgtgtccc tacctcctcc tctggacaaa gcgttcactc ccaacctgac                   911

<210> SEQ ID NO 14
<211> LENGTH: 205
<212> TYPE: PRT
<213> ORGANISM: Artificial Sequence
<220> FEATURE:
<223> OTHER INFORMATION: Description of Artificial Sequence:  Synthetic
      Primer

<400> SEQUENCE: 14

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
 65                 70                  75                  80

Ala Ala Gly Pro Ala Leu Ser Pro Val Pro Pro Val His Leu Ala Leu
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160
```

```
-continued

Ser Val Asn Arg Glu Met Ser Pro Leu Val Asp Asn Ile Ala Leu Trp
            165                 170                 175

Met Thr Glu Tyr Leu Asn Arg His Leu His Thr Trp Ile Gln Asp Asn
            180                 185                 190

Gly Gly Trp Val Gly Ala Ser Gly Asp Val Ser Leu Gly
            195                 200                 205
```